(12) United States Patent  
Dai

(10) Patent No.: US 9,642,518 B2  
(45) Date of Patent: May 9, 2017

(54) RANDOM EYE GENERATION SYSTEMS AND METHODS

(71) Applicant: AMO Development, LLC, Santa Ana, CA (US)

(72) Inventor: Guang-ming Dai, Fremont, CA (US)

(73) Assignee: AMO Development, LLC, Santa Ana, CA (US)

( * ) Notice: Subject to any disclaimer, the term of this patent is extended or adjusted under 35 U.S.C. 154(b) by 433 days.

(21) Appl. No.: 14/097,787

(22) Filed: Dec. 5, 2013

(65) Prior Publication Data

US 2014/0160437 A1 Jun. 12, 2014

Related U.S. Application Data

(60) Provisional application No. 61/734,081, filed on Dec. 6, 2012.

(51) Int. Cl.
 *A61B 3/00* (2006.01)

(52) U.S. Cl.
 CPC ................. *A61B 3/0025* (2013.01)

(58) Field of Classification Search
 CPC ....... A61B 3/1015; A61B 3/0025; A61B 3/02; A61B 3/024; A61B 5/4836
 USPC .................................................. 351/200–247
 See application file for complete search history.

(56) References Cited

U.S. PATENT DOCUMENTS

| | | |
|---|---|---|
| 4,665,913 A | 5/1987 | L'Esperance, Jr. |
| 4,669,466 A | 6/1987 | L'Esperance |
| 4,732,148 A | 3/1988 | L'Esperance, Jr. |
| 4,770,172 A | 9/1988 | L'Esperance, Jr. |
| 4,773,414 A | 9/1988 | L'Esperance, Jr. |
| 5,108,388 A | 4/1992 | Trokel et al. |
| 5,163,934 A | 11/1992 | Munnerlyn |
| 5,207,668 A | 5/1993 | L'Esperance, Jr. |
| 5,219,343 A | 6/1993 | L'Esperance, Jr. |
| 5,646,791 A | 7/1997 | Glockler |
| 5,683,379 A | 11/1997 | Hohla |
| 5,713,892 A | 2/1998 | Shimmick |
| 5,807,379 A | 9/1998 | L'Esperance, Jr. |
| 6,004,313 A | 12/1999 | Shimmick et al. |
| 6,095,651 A | 8/2000 | Williams et al. |
| 6,203,539 B1 | 3/2001 | Shimmick et al. |

(Continued)

FOREIGN PATENT DOCUMENTS

| | | |
|---|---|---|
| DE | 102005006897 A1 | 8/2006 |
| WO | 0207660 A2 | 1/2002 |

(Continued)

OTHER PUBLICATIONS

"Monte Carlo Simulation." Palisade. N.p., Mar. 14, 2008. Web. Jan. 11, 2016.*

(Continued)

*Primary Examiner* — Mahidere Sahle
(74) *Attorney, Agent, or Firm* — Abbott Medical Optics Inc.

(57) ABSTRACT

Random human eye generators are provided for use in evaluating aspects of treatment in refractive surgery or other therapeutic vision modalities. Exemplary random eye generators include an optical parameter such as a manifest refractive sphere parameter or a wavefront sphere parameter, and incorporate a Rayleigh distribution for such parameters.

24 Claims, 19 Drawing Sheets

(56) References Cited

U.S. PATENT DOCUMENTS

| | | |
|---|---|---|
| 6,245,059 B1 | 6/2001 | Clapham |
| 6,271,915 B1 | 8/2001 | Frey et al. |
| 6,315,413 B1 | 11/2001 | Shimmick et al. |
| 6,331,177 B1 | 12/2001 | Munnerlyn et al. |
| 6,428,533 B1 | 8/2002 | Bille |
| 6,547,393 B2 | 4/2003 | Ruiz |
| 6,887,232 B2 | 5/2005 | Bille |
| 7,232,436 B2 | 6/2007 | Bille |
| 7,273,277 B2 | 9/2007 | Sarver |
| 7,296,893 B2 | 11/2007 | Dai |
| 7,460,288 B2 | 12/2008 | Liang |
| 7,926,490 B2 | 4/2011 | Dai et al. |
| 8,409,178 B2 | 4/2013 | Dai et al. |
| 8,663,207 B2 | 3/2014 | Dai et al. |
| 2003/0053030 A1 | 3/2003 | Levine |
| 2005/0096640 A1 | 5/2005 | Dai et al. |
| 2005/0107775 A1 | 5/2005 | Huang et al. |
| 2006/0173445 A1 | 8/2006 | Bille |
| 2007/0222948 A1 | 9/2007 | Dai |
| 2008/0033408 A1 | 2/2008 | Bueler et al. |
| 2008/0058778 A1 | 3/2008 | Liedel et al. |
| 2009/0171871 A1* | 7/2009 | Zhang .................. G06F 19/345 706/12 |
| 2010/0114076 A1 | 5/2010 | Reinstein et al. |
| 2011/0166558 A1 | 7/2011 | Dai et al. |
| 2011/0246165 A1 | 10/2011 | Dai et al. |
| 2013/0100410 A1 | 4/2013 | Liang |
| 2013/0190736 A1 | 7/2013 | Fabrikant et al. |
| 2014/0095137 A1 | 4/2014 | Dai et al. |

FOREIGN PATENT DOCUMENTS

| | | |
|---|---|---|
| WO | 2010049157 A1 | 5/2010 |
| WO | 2014055690 A1 | 4/2014 |

OTHER PUBLICATIONS

"Rayleigh Disribution." Wikipedia. Wikimedia Foundation, Apr. 18, 2005. Web. 11 Jan. 11, 2016.*
Co-pending U.S. Appl. No. 14/453,068, filed Aug. 6, 2014.
Huang D., et al., "Mathematical Model of Corneal Surface Smoothing After Laser Refractive Surgery," American Journal of Ophthalmology, 2003, vol. 135 (3), pp. 267-278.
International Search Report and Written Opinion for Application No. PCT/US2011/030570, mailed on Aug. 10, 2011, 13 pages.
International Search Report and Written Opinion for Application No. PCT/US2014/064678, mailed on Feb. 9, 2015, 11 pages.

* cited by examiner

RANDOM EYE GENERATION SYSTEMS AND METHODS

CROSS-REFERENCES TO RELATED APPLICATIONS

This application is a non-provisional of and claims the benefit of priority to U.S. Provisional Patent Application No. 61/734,081 filed Dec. 6, 2012. This application is also related to U.S. patent application Ser. No. 12/749,751 filed Mar. 30, 2010. The entire content of each of the above filings is incorporated herein by reference.

BACKGROUND OF THE INVENTION

Embodiments of the present invention relate generally to the field of vision treatment, and in particular encompass systems and methods for simulating random human eyes for use in evaluating aspects of treatment in refractive surgery or other therapeutic vision modalities.

Various eye models have been proposed to simulate vision characteristics of the eye, or to predict the effect of certain vision treatments. Although such techniques may be helpful in advancing the state of patient eye care, still further improvements are desired. Embodiments of the present invention address these and other outstanding needs.

BRIEF SUMMARY OF THE INVENTION

Exemplary random eye models can be used to generate a large number of eyes, so that the statistical parameters of those eyes match the statistics of eyes from certain populations. For example, random eye generators can operate to provide random eyes with statistical parameters which correspond to those of the general population. Relatedly, random eye generators can operate to provide random eyes with statistical parameters which correspond to those of a refractive surgery population. In some instances, the statistical parameters correspond to particular surgical parameters.

Random eye generation models can be used for a variety of purposes. For example, random eye models can be used for verification and validation (V & V) techniques involving a large number of eyes at different refractive ranges. Further, random eye models can be used to simulate clinical trials for testing possible ablation characteristics of a particular treatment design or correction modality. Random eye models can also be used to refine treatment algorithms which may benefit from a large number of eyes to achieve statistical significance where a high degree of noise level may be problematic.

In some instances, random eye generation mechanisms can be used in combination with other validated mechanisms such as target controller mechanisms and virtual ablation mechanisms, so as to perform "real-life" validation similar to a virtual clinical trial. Often, such validated mechanisms can be provided as modules such as software and/or hardware modules. In some instances, these validated mechanisms or modules can be based on MATLAB protocols. For example, a target controller mechanism or module can involve or approximate a production C++ code for creating treatment targets. In some instances, a target controller mechanism may approximate such a production code within a difference that is in the order of nanometers, or 10 to −3 microns, or lower. Similarly, a virtual ablation mechanism or module can involve or approximate a production C++ code for simulating laser pulse delivery. In some instances, a virtual ablation mechanism may approximate such a production code within a difference that is in the order of nanometers, or 10 to −3 microns, or lower. In some embodiments, environmental issues, biological effects, human (e.g. patient or surgeon) effects can be ignored or disregarded. A random eye mechanism can be used to generate "real-life" patients (in terms of eyes) to be considered as an input to a production code. Thus, it is possible to do software verification and validation (V & V) or even a "virtual clinical trial" to evaluate safety and efficacy issues. For example, a random eye generator can be used in conjunction with a target controller mechanism and a virtual ablation mechanism (i.e. validated mechanisms which approximate production code implementations) as discussed elsewhere herein.

In a first aspect, embodiments of the present invention encompass systems and methods for evaluating a vision treatment protocol. Exemplary methods may include obtaining the vision treatment protocol, obtaining a random eye generator, and evaluating the vision treatment protocol using the random eye generator. The random eye generator can include a first optical parameter, and the random eye generator can have a Rayleigh distribution for the first optical parameter. In some cases, the first optical parameter can be a manifest refractive sphere parameter or a wavefront sphere parameter. In some cases, the first optical parameter is a wavefront sphere parameter, and the wavefront sphere parameter is based on a manifest refractive sphere parameter having a Rayleigh distribution plus a random number parameter having a normal distribution. In some cases, the random eye generator further includes a second optical parameter, and the random eye generator has a normal distribution for the second optical parameter. In some cases, the second optical parameter is a manifest refractive cylinder parameter, a wavefront cylinder parameter, a keratometry parameter, a pachymetry parameter, a wavefront diameter parameter, or a high order aberration parameter. In some cases, the second optical parameter is a wavefront cylinder parameter, and the wavefront cylinder parameter is based on a manifest refractive cylinder parameter having a normal distribution plus a random number parameter having a normal distribution. In some cases, the random eye generator further includes second optical parameter, and the random eye generator has a uniform distribution for the second optical parameter. In some cases, the second optical parameter includes a manifest refractive cylinder axis parameter and a wavefront cylinder axis parameter. In some cases, the second optical parameter includes a wavefront cylinder parameter, and the wavefront cylinder parameter is based on a manifest refractive cylinder parameter having a uniform distribution plus a random number parameter having a normal distribution. In some cases, methods may include verifying the vision treatment protocol based on the evaluation.

In another aspect, embodiments of the present invention encompass systems and methods for modifying a vision treatment protocol. Exemplary methods may include obtaining the vision treatment protocol, obtaining a random eye generator, and modifying the vision treatment protocol using the random eye generator. The random eye generator can include a first optical parameter, and the random eye generator can have a Rayleigh distribution for the first optical parameter.

In still another aspect, embodiments of the present invention encompass systems and methods for evaluating a vision treatment protocol. Exemplary systems may include a processor and one or more modules. For example, a system may include a processor, a first module having a tangible medium embodying machine-readable code executed on the processor to receive the vision treatment protocol, a second module having a tangible medium embodying machine-readable code executed on the processor to receive a random eye generator that includes a first optical parameter, where the random eye generator has a Rayleigh distribution for the first optical parameter, and a third module having a tangible medium embodying machine-readable code executed on the processor to evaluate the vision treatment protocol using the random eye generator. In some cases, systems may include a fourth module having a tangible medium embodying machine-readable code executed on the processor to verify the vision treatment protocol based on the evaluation. In some cases, the first optical parameter includes a manifest refractive sphere parameter or a wavefront sphere parameter. In some cases, the first optical parameter includes a wavefront sphere parameter, and the wavefront sphere parameter is based on a manifest refractive sphere parameter having a Rayleigh distribution plus a random number parameter having a normal distribution. In some cases, the random eye generator also includes a second optical parameter, and the random eye generator has a normal distribution for the second optical parameter. In some cases, the second optical parameter includes a manifest refractive cylinder parameter, a wavefront cylinder parameter, a keratometry parameter, a pachymetry parameter, a wavefront diameter parameter, or a high order aberration parameter. In some cases, the second optical parameter includes a wavefront cylinder parameter, and the wavefront cylinder parameter is based on a manifest refractive cylinder parameter having a normal distribution plus a random number parameter having a normal distribution. In some cases, the random eye generator also includes a second optical parameter, and the random eye generator has a uniform distribution for the second optical parameter. In some cases, the second optical parameter includes a manifest refractive cylinder axis parameter or a wavefront cylinder axis parameter.

DETAILED DESCRIPTION OF THE INVENTION

Figure 1:
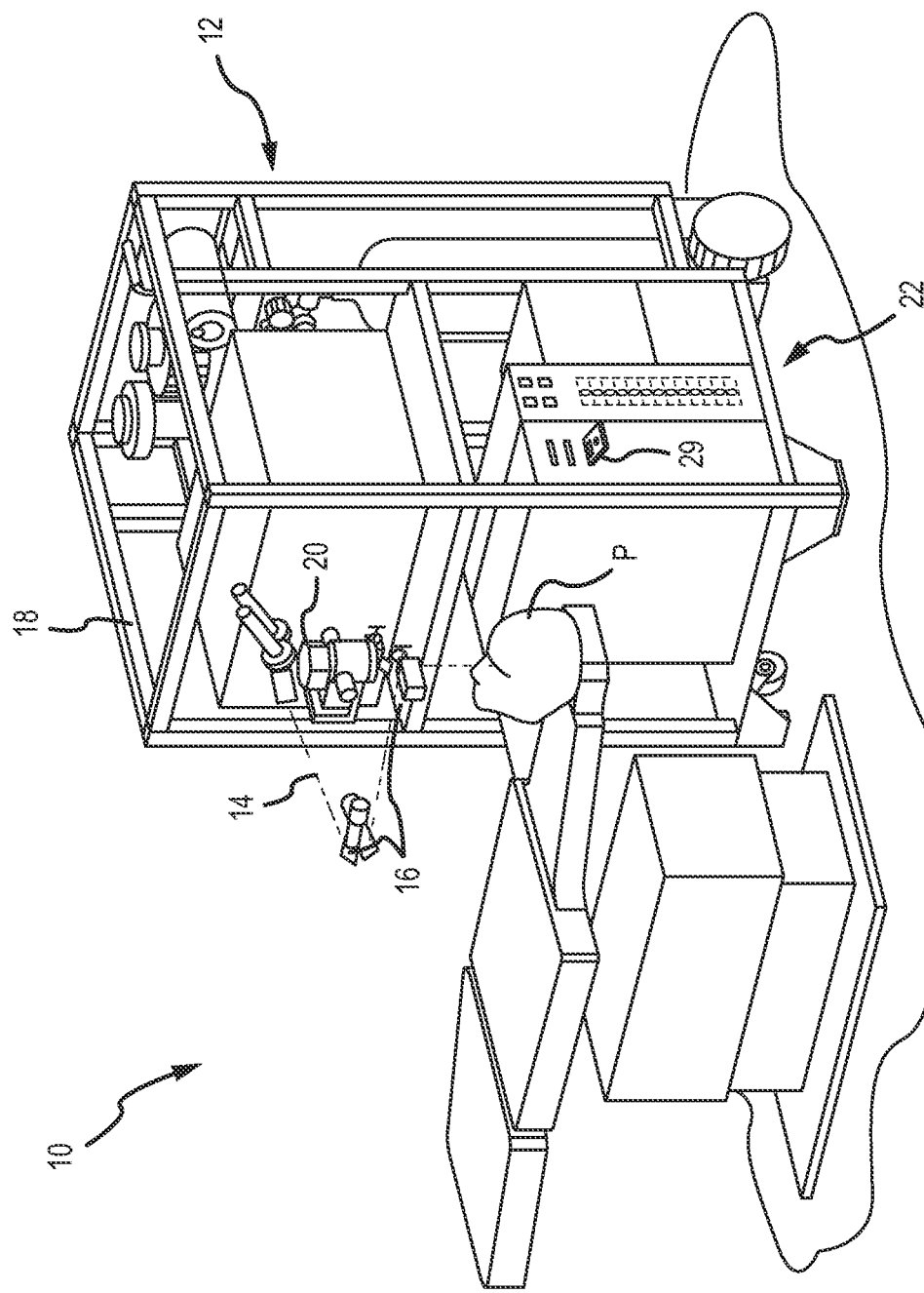
FIG. 1 illustrates a laser ablation system according to an embodiment of the present invention.

Embodiments of the present invention encompass a variety of techniques for generating human eyes for use in refractive surgery development. Exemplary systems and methods involve simulating or generating random human eyes for use in evaluating ablations for refractive surgery. Performance of a "virtual ablation" may involve a variety of surgical parameters, such as ocular aberrations, manifest refractions, keratometry, pachymetry, optical zone, ablation zone, and the like.

According to some embodiments, it is possible to develop random eye generators based on population data from medical surveys. Such random eye generators can be used to evaluate and develop laser refractive surgery techniques, and other vision correction modalities including contact lenses, spectacle lenses, intraocular lenses, and the like. The random eye models can generate any desired number of model eyes, to cover any of a variety of refractive cases.

During the software verification and validation (V & V), oftentimes a handful of surgical parameter combinations can be used to test the functionality of existing and newly introduced algorithms. With black box testing through user interface (UI), it is may be difficult to identify software bugs or design flaws because exhaustive testing may be difficult or impossible. On the other hand, using validated MATLAB software tools, such as a target controller mechanism and a virtual ablation mechanism, it is possible to perform evaluations using a large number of eyes. Random eye generation or simulation mechanisms are also helpful for bulk testing or evaluation. For example, a random eye generation or simulation mechanism can be used to generate a large number of eyes (e.g. randomly), such that the statistics of the eyes match the statistics of the general population for a particular surgical parameter. For example, this may involve determining the manifest refraction, keratometry, pachymetry, ocular aberrations, and optical and ablation zones for individual random eyes.

Embodiments of the present invention can be readily adapted for use with existing laser systems and other optical treatment devices. Although system, software, and method embodiments of the present invention are described primarily in the context of a laser eye surgery system, it should be understood that embodiments of the present invention may be adapted for use in or in combination with alternative eye treatment procedures, systems, or modalities, such as spectacle lenses, intraocular lenses, accommodating IOLs, contact lenses, corneal ring implants, collagenous corneal tissue thermal remodeling, corneal inlays, corneal onlays, other corneal implants or grafts, and the like. Relatedly, systems, software, and methods according to embodiments of the present invention are well suited for customizing any of these treatment modalities to a specific patient. Thus, for example, embodiments encompass custom preformed lenses, intraocular lenses, custom contact lenses, custom corneal implants, and the like, which can be configured to treat or ameliorate any of a variety of vision conditions in a particular patient based on their unique ocular characteristics or anatomy. Additionally, the modified ablation target or target shape may be implemented via other non-ablative laser therapies, such as laser-incised custom lenticule shapes and subsequent extraction and laser-based corneal incision patterns.

In some instances, these techniques can be carried out in conjunction with treatments provided by any of a variety of laser devices, including without limitation the WaveScan® System and the STAR S4® Excimer Laser System both by Abbott Medical Optics Inc., the WaveLight® Allegretto Wave® Eye-Q laser, the Schwind Amaris™ lasers, the 217P excimer workstation by Technolas PerfectVision GmbH, the Mel 80™ laser by Carl Zeiss Meditec, Inc., and the like. In some cases, embodiments provide techniques for using laser basis data during refractive surgery treatment procedures which can be implemented in such laser devices.

Turning now to the drawings, FIG. 1 illustrates a laser eye surgery system 10 of the present invention, including a laser 12 that produces a laser beam 14. Laser 12 is optically coupled to laser delivery optics 16, which directs laser beam 14 to an eye E of patient P. A delivery optics support structure (not shown here for clarity) extends from a frame 18 supporting laser 12. A microscope 20 is mounted on the delivery optics support structure, the microscope often being used to image a cornea of eye E.

Laser 12 generally comprises an excimer laser, ideally comprising an argon-fluorine laser producing pulses of laser light having a wavelength of approximately 193 nm. Laser 12 will preferably be designed to provide a feedback stabilized fluence at the patient's eye, delivered via delivery optics 16. The present invention may also be useful with alternative sources of ultraviolet or infrared radiation, particularly those adapted to controllably ablate the corneal tissue without causing significant damage to adjacent and/or underlying tissues of the eye. Such sources include, but are not limited to, solid state lasers and other devices which can generate energy in the ultraviolet wavelength between about 185 and 205 nm and/or those which utilize frequency-multiplying techniques. Hence, although an excimer laser is the illustrative source of an ablating beam, other lasers may be used in the present invention.

Laser system 10 will generally include a computer or programmable processor 22. Processor 22 may comprise (or interface with) a conventional PC system including the standard user interface devices such as a keyboard, a display monitor, and the like. Processor 22 will typically include an input device such as a magnetic or optical disk drive, an internet connection, or the like. Such input devices will often be used to download a computer executable code from a tangible storage media 29 embodying any of the methods of the present invention. Tangible storage media 29 may take the form of a floppy disk, an optical disk, a data tape, a volatile or non-volatile memory, RAM, or the like, and the processor 22 will include the memory boards and other standard components of modern computer systems for storing and executing this code. Tangible storage media 29 may optionally embody wavefront sensor data, wavefront gradients, a wavefront elevation map, a treatment map, a corneal elevation map, and/or an ablation table. While tangible storage media 29 will often be used directly in cooperation with an input device of processor 22, the storage media may also be remotely operatively coupled with processor by means of network connections such as the internet, and by wireless methods such as infrared, Bluetooth, or the like.

Laser 12 and delivery optics 16 will generally direct laser beam 14 to the eye of patient P under the direction of a computer 22. Computer 22 will often selectively adjust laser beam 14 to expose portions of the cornea to the pulses of laser energy so as to effect a predetermined sculpting of the cornea and alter the refractive characteristics of the eye. In many embodiments, both laser beam 14 and the laser delivery optical system 16 will be under computer control of processor 22 to effect the desired laser sculpting process, with the processor effecting (and optionally modifying) the pattern of laser pulses. The pattern of pulses may by summarized in machine readable data of tangible storage media 29 in the form of a treatment table, and the treatment table may be adjusted according to feedback input into processor 22 from an automated image analysis system in response to feedback data provided from an ablation monitoring system feedback system. Optionally, the feedback may be manually entered into the processor by a system operator. Such feedback might be provided by integrating the wavefront measurement system described below with the laser treatment system 10, and processor 22 may continue and/or terminate a sculpting treatment in response to the feedback, and may optionally also modify the planned sculpting based at least in part on the feedback. Measurement systems are further described in U.S. Pat. No. 6,315,413, the full disclosure of which is incorporated herein by reference.

Laser beam 14 may be adjusted to produce the desired sculpting using a variety of alternative mechanisms. The laser beam 14 may be selectively limited using one or more variable apertures. An exemplary variable aperture system having a variable iris and a variable width slit is described in U.S. Pat. No. 5,713,892, the full disclosure of which is incorporated herein by reference. The laser beam may also be tailored by varying the size and offset of the laser spot from an axis of the eye, as described in U.S. Pat. Nos. 5,683,379, 6,203,539, and 6,331,177, the full disclosures of which are incorporated herein by reference.

Still further alternatives are possible, including scanning of the laser beam over the surface of the eye and controlling the number of pulses and/or dwell time at each location, as described, for example, by U.S. Pat. No. 4,665,913, the full disclosure of which is incorporated herein by reference; using masks in the optical path of laser beam 14 which ablate to vary the profile of the beam incident on the cornea, as described in U.S. Pat. No. 5,807,379, the full disclosure of which is incorporated herein by reference; hybrid profile-scanning systems in which a variable size beam (typically controlled by a variable width slit and/or variable diameter iris diaphragm) is scanned across the cornea; or the like. The computer programs and control methodology for these laser pattern tailoring techniques are well described in the patent literature.

Additional components and subsystems may be included with laser system 10, as should be understood by those of skill in the art. For example, spatial and/or temporal integrators may be included to control the distribution of energy within the laser beam, as described in U.S. Pat. No. 5,646,791, the full disclosure of which is incorporated herein by reference. Ablation effluent evacuators/filters, aspirators, and other ancillary components of the laser surgery system are known in the art. Further details of suitable systems for performing a laser ablation procedure can be found in commonly assigned U.S. Pat. Nos. 4,665,913, 4,669,466, 4,732,148, 4,770,172, 4,773,414, 5,207,668, 5,108,388, 5,219,343, 5,646,791 and 5,163,934, the complete disclosures of which are incorporated herein by reference. Suitable systems also include commercially available refractive laser systems such as those manufactured and/or sold by Alcon, Bausch & Lomb, Nidek, WaveLight, LaserSight, Schwind, Zeiss-Meditec, and the like. Basis data can be further characterized for particular lasers or operating conditions, by taking into account localized environmental variables such as temperature, humidity, airflow, and aspiration.

Figure 2:
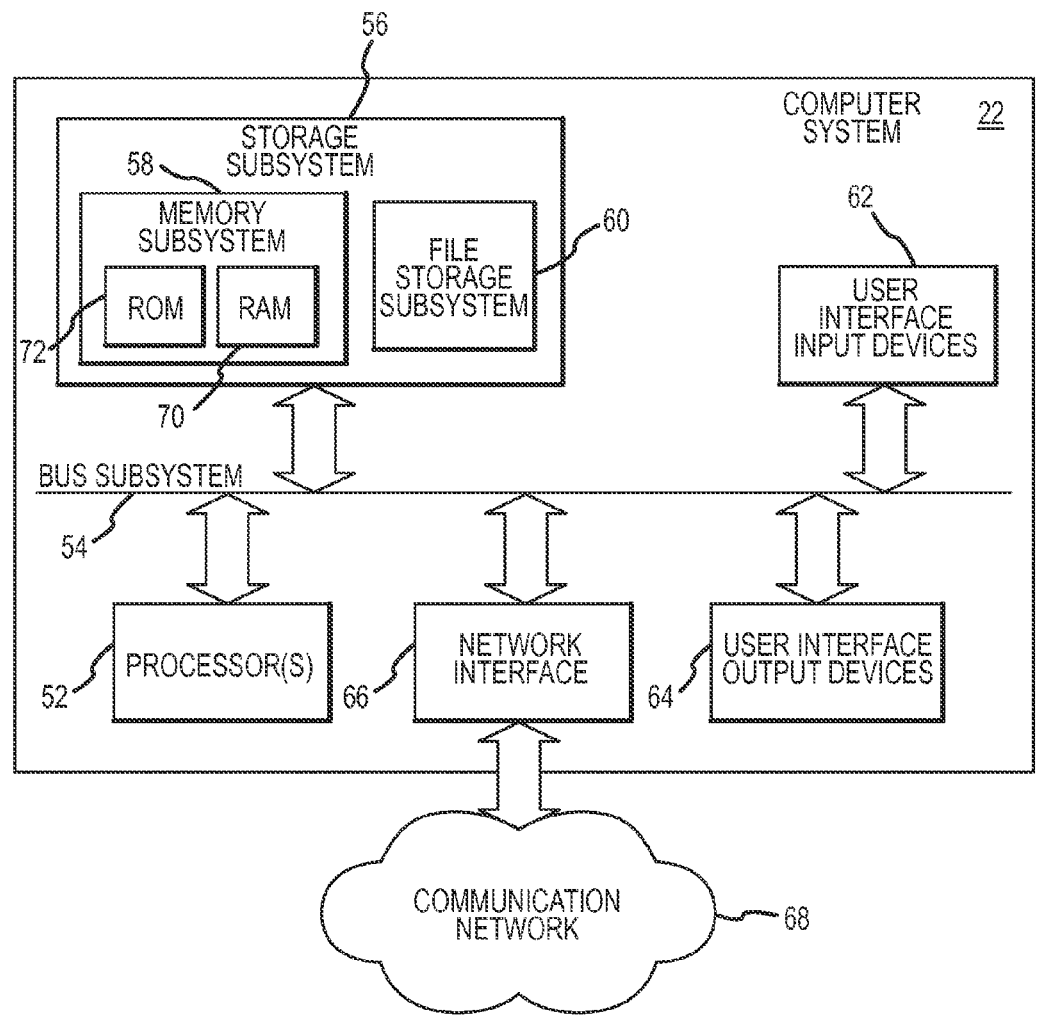
FIG. 2 illustrates a simplified computer system according to an embodiment of the present invention.

FIG. 2 is a simplified block diagram of an exemplary computer system 22 that may be used by the laser surgical system 10 of the present invention. Computer system 22 typically includes at least one processor 52 which may communicate with a number of peripheral devices via a bus subsystem 54. These peripheral devices may include a storage subsystem 56, comprising a memory subsystem 58 and a file storage subsystem 60, user interface input devices 62, user interface output devices 64, and a network interface subsystem 66. Network interface subsystem 66 provides an interface to outside networks 68 and/or other devices, such as the wavefront measurement system 30.

User interface input devices 62 may include a keyboard, pointing devices such as a mouse, trackball, touch pad, or graphics tablet, a scanner, foot pedals, a joystick, a touchscreen incorporated into the display, audio input devices such as voice recognition systems, microphones, and other types of input devices. User input devices 62 will often be used to download a computer executable code from a tangible storage media 29 embodying any of the methods of the present invention. In general, use of the term "input device" is intended to include a variety of conventional and proprietary devices and ways to input information into computer system 22.

User interface output devices 64 may include a display subsystem, a printer, a fax machine, or non-visual displays such as audio output devices. The display subsystem may be a cathode ray tube (CRT), a flat-panel device such as a liquid crystal display (LCD), a projection device, or the like. The display subsystem may also provide a non-visual display such as via audio output devices. In general, use of the term "output device" is intended to include a variety of conventional and proprietary devices and ways to output information from computer system 22 to a user.

Storage subsystem 56 can store the basic programming and data constructs that provide the functionality of the various embodiments of the present invention. For example, a database and modules implementing the functionality of the methods of the present invention, as described herein, may be stored in storage subsystem 56. These software modules are generally executed by processor 52. In a distributed environment, the software modules may be stored on a plurality of computer systems and executed by processors of the plurality of computer systems. Storage subsystem 56 typically comprises memory subsystem 58 and file storage subsystem 60.

Memory subsystem 58 typically includes a number of memories including a main random access memory (RAM) 70 for storage of instructions and data during program execution and a read only memory (ROM) 72 in which fixed instructions are stored. File storage subsystem 60 provides persistent (non-volatile) storage for program and data files, and may include tangible storage media 29 (FIG. 1) which may optionally embody wavefront sensor data, wavefront gradients, a wavefront elevation map, a treatment map, and/or an ablation table. File storage subsystem 60 may include a hard disk drive, a floppy disk drive along with associated removable media, a Compact Digital Read Only Memory (CD-ROM) drive, an optical drive, DVD, CD-R, CD-RW, solid-state removable memory, and/or other removable media cartridges or disks. One or more of the drives may be located at remote locations on other connected computers at other sites coupled to computer system 22. The modules implementing the functionality of the present invention may be stored by file storage subsystem 60.

Bus subsystem 54 provides a mechanism for letting the various components and subsystems of computer system 22 communicate with each other as intended. The various subsystems and components of computer system 22 need not be at the same physical location but may be distributed at various locations within a distributed network. Although bus subsystem 54 is shown schematically as a single bus, alternate embodiments of the bus subsystem may utilize multiple busses.

Computer system 22 itself can be of varying types including a personal computer, a portable computer, a workstation, a computer terminal, a network computer, a control system in a wavefront measurement system or laser surgical system, a mainframe, or any other data processing system. Due to the ever-changing nature of computers and networks, the description of computer system 22 depicted in FIG. 2 is intended only as a specific example for purposes of illustrating one embodiment of the present invention. Many other configurations of computer system 22 are possible having more or less components than the computer system depicted in FIG. 2.

Figure 3:
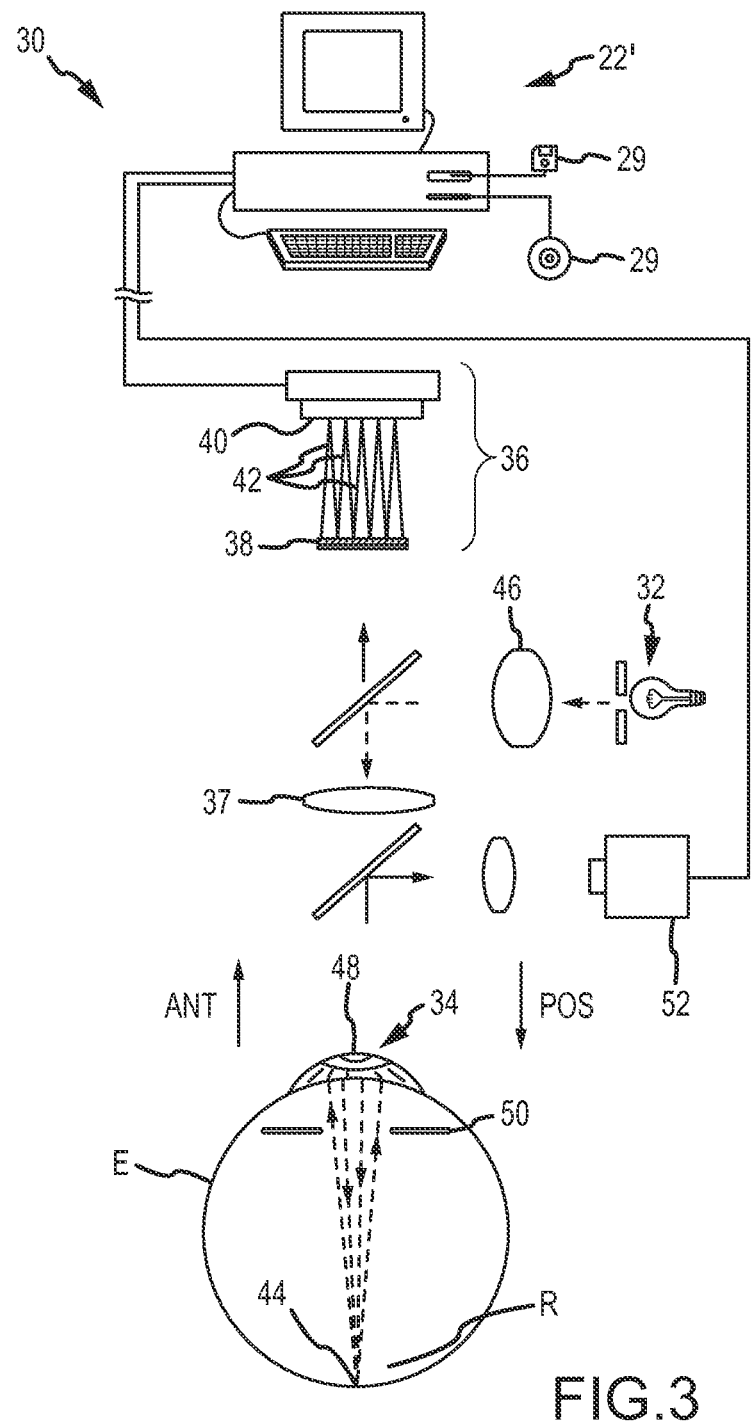
FIG. 3 illustrates a wavefront measurement system according to an embodiment of the present invention.

Referring now to FIG. 3, one embodiment of a wavefront measurement system 30 is schematically illustrated in simplified form. In very general terms, wavefront measurement system 30 is configured to sense local slopes of a gradient map exiting the patient's eye. Devices based on the Hartmann-Shack principle generally include a lenslet array to sample the gradient map uniformly over an aperture, which is typically the exit pupil of the eye. Thereafter, the local slopes of the gradient map are analyzed so as to reconstruct the wavefront surface or map.

More specifically, one wavefront measurement system 30 includes an image source 32, such as a laser, which projects a source image through optical tissues 34 of eye E so as to form an image 44 upon a surface of retina R. The image from retina R is transmitted by the optical system of the eye (e.g., optical tissues 34) and imaged onto a wavefront sensor 36 by system optics 37. The wavefront sensor 36 communicates signals to a computer system 22' for measurement of the optical errors in the optical tissues 34 and/or determination of an optical tissue ablation treatment program. Computer 22' may include the same or similar hardware as the computer system 22 illustrated in FIGS. 1 and 2. Computer system 22' may be in communication with computer system 22 that directs the laser surgery system 10, or some or all of the components of computer system 22, 22' of the wavefront measurement system 30 and laser surgery system 10 may be combined or separate. If desired, data from wavefront sensor 36 may be transmitted to a laser computer system 22 via tangible media 29, via an I/O port, via an networking connection 66 such as an intranet or the Internet, or the like.

Wavefront sensor 36 generally comprises a lenslet array 38 and an image sensor 40. As the image from retina R is transmitted through optical tissues 34 and imaged onto a surface of image sensor 40 and an image of the eye pupil P is similarly imaged onto a surface of lenslet array 38, the lenslet array separates the transmitted image into an array of beamlets 42, and (in combination with other optical components of the system) images the separated beamlets on the surface of sensor 40. Sensor 40 typically comprises a charged couple device or "CCD," and senses the characteristics of these individual beamlets, which can be used to determine the characteristics of an associated region of optical tissues 34. In particular, where image 44 comprises a point or small spot of light, a location of the transmitted spot as imaged by a beamlet can directly indicate a local gradient of the associated region of optical tissue.

Eye E generally defines an anterior orientation ANT and a posterior orientation POS. Image source 32 generally projects an image in a posterior orientation through optical tissues 34 onto retina R as indicated in FIG. 3. Optical tissues 34 again transmit image 44 from the retina anteriorly toward wavefront sensor 36. Image 44 actually formed on retina R may be distorted by any imperfections in the eye's optical system when the image source is originally transmitted by optical tissues 34. Optionally, image source projection optics 46 may be configured or adapted to decrease any distortion of image 44.

In some embodiments, image source optics 46 may decrease lower order optical errors by compensating for spherical and/or cylindrical errors of optical tissues 34. Higher order optical errors of the optical tissues may also be compensated through the use of an adaptive optic element, such as a deformable mirror (described below). Use of an image source 32 selected to define a point or small spot at image 44 upon retina R may facilitate the analysis of the data provided by wavefront sensor 36. Distortion of image 44 may be limited by transmitting a source image through a central region 48 of optical tissues 34 which is smaller than a pupil 50, as the central portion of the pupil may be less prone to optical errors than the peripheral portion. Regardless of the particular image source structure, it will be generally be beneficial to have a well-defined and accurately formed image 44 on retina R.

In one embodiment, the wavefront data may be stored in a computer readable medium 29 or a memory of the wavefront sensor system 30 in two separate arrays containing the x and y wavefront gradient values obtained from image spot analysis of the Hartmann-Shack sensor images, plus the x and y pupil center offsets from the nominal center of the Hartmann-Shack lenslet array, as measured by the pupil camera 51 (FIG. 3) image. Such information contains all the available information on the wavefront error of the eye and is sufficient to reconstruct the wavefront or any portion of it. In such embodiments, there is no need to reprocess the Hartmann-Shack image more than once, and the data space required to store the gradient array is not large. For example, to accommodate an image of a pupil with an 8 mm diameter, an array of a 20×20 size (i.e., 400 elements) is often sufficient. As can be appreciated, in other embodiments, the wavefront data may be stored in a memory of the wavefront sensor system in a single array or multiple arrays.

While the methods of the present invention will generally be described with reference to sensing of an image 44, it should be understood that a series of wavefront sensor data readings may be taken. For example, a time series of wavefront data readings may help to provide a more accurate overall determination of the ocular tissue aberrations. As the ocular tissues can vary in shape over a brief period of time, a plurality of temporally separated wavefront sensor measurements can avoid relying on a single snapshot of the optical characteristics as the basis for a refractive correcting procedure. Still further alternatives are also available, including taking wavefront sensor data of the eye with the eye in differing configurations, positions, and/or orientations. For example, a patient will often help maintain alignment of the eye with wavefront measurement system 30 by focusing on a fixation target, as described in U.S. Pat. No. 6,004,313, the full disclosure of which is incorporated herein by reference. By varying a position of the fixation target as described in that reference, optical characteristics of the eye may be determined while the eye accommodates or adapts to image a field of view at a varying distance and/or angles.

The location of the optical axis of the eye may be verified by reference to the data provided from a pupil camera 52. In the exemplary embodiment, a pupil camera 52 images pupil 50 so as to determine a position of the pupil for registration of the wavefront sensor data relative to the optical tissues.

Figure 3A:
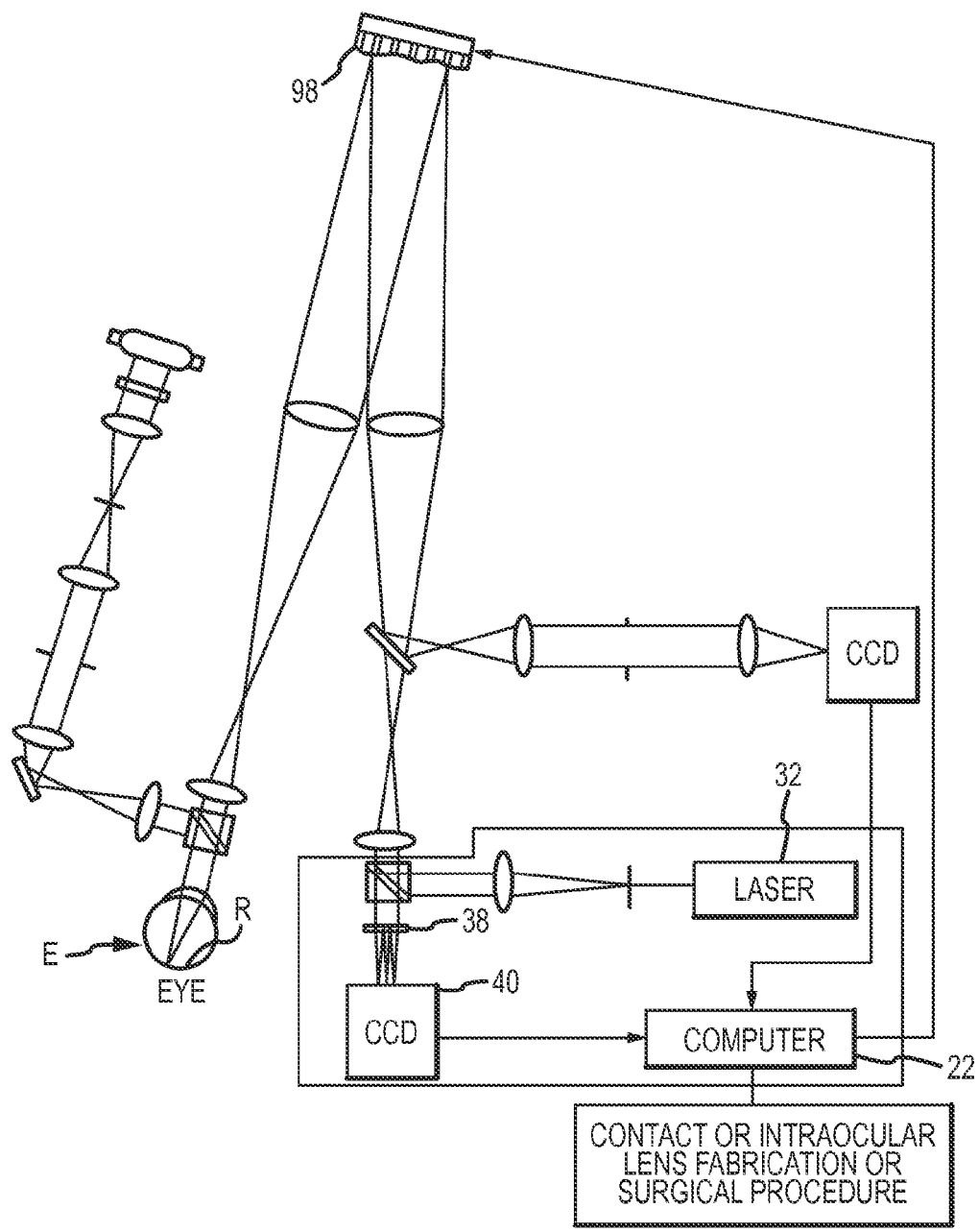
FIG. 3A illustrates another wavefront measurement system according to an embodiment of the present invention.

An alternative embodiment of a wavefront measurement system is illustrated in FIG. 3A. The major components of the system of FIG. 3A are similar to those of FIG. 3. Additionally, FIG. 3A includes an adaptive optical element 53 in the form of a deformable mirror. The source image is reflected from deformable mirror 98 during transmission to retina R, and the deformable mirror is also along the optical path used to form the transmitted image between retina R and imaging sensor 40. Deformable mirror 98 can be controllably deformed by computer system 22 to limit distortion of the image formed on the retina or of subsequent images formed of the images formed on the retina, and may enhance the accuracy of the resultant wavefront data. The structure and use of the system of FIG. 3A are more fully described in U.S. Pat. No. 6,095,651, the full disclosure of which is incorporated herein by reference.

The components of an embodiment of a wavefront measurement system for measuring the eye and ablations may comprise elements of a WaveScan® system, available from AMO Manufacturing USA, LLC, Milpitas, Calif. One embodiment includes a WaveScan system with a deformable mirror as described above. An alternate embodiment of a wavefront measuring system is described in U.S. Pat. No. 6,271,915, the full disclosure of which is incorporated herein by reference. It is appreciated that any wavefront aberrometer could be employed for use with the present invention. Relatedly, embodiments of the present invention encompass the implementation of any of a variety of optical instruments provided by Abbott Medical Optics, Inc., including the iDesign system, and the like.

Relatedly, embodiments of the present invention encompass the implementation of any of a variety of optical instruments provided by WaveFront Sciences, Inc., including the COAS wavefront aberrometer, the ClearWave contact lens aberrometer, the CrystalWave IOL aberrometer, and the like. Embodiments of the present invention may also involve wavefront measurement schemes such as a Tscherning-based system, which may be provided by WaveFront Sciences, Inc. Embodiments of the present invention may also involve wavefront measurement schemes such as a ray tracing-based system, which may be provided by Tracey Technologies, Corp.

Optical Parameters and Distributions

Embodiments of the present invention encompass systems and methods for evaluating vision treatment protocols. For example, a random eye generator can be used to evaluate such, such vision treatment protocols are evaluated by using a random eye generator. Typically, the random eye generator includes one or more optical parameters, each parameter having a certain distribution. For example, as discussed elsewhere herein, a random eye generator may include a sphere power optical parameter having a Rayleigh distribution.

In some cases, an optical parameter may include a sphere parameter (e.g. manifest refractive sphere power or wavefront sphere), a cylinder parameter (e.g. manifest refractive cylinder power or wavefront cylinder), an axis parameter (e.g. cylinder axis), a keratometry parameter, a population parameter, a wavefront diameter parameter, a high order aberration parameter, and the like. In some cases, optical parameters can be based on Zernike values (e.g. wavefront data). In some cases, optical parameters can be based on refractive values (e.g. non-wavefront or manifest refraction data).

Population data was obtained from US surveys performed for 393,139,704 eyes. For this general population, it was discovered that the probability of the manifest refractive sphere (MRS) for both myopia and hyperopia followed a normal distribution, with the standard deviation of 3.65 D for myopia and 3.3 D for hyperopia and a sub-population ratio of 63.65% for myopia versus 36.35% for hyperopia.

Further, laser vision correction (LVC) candidate data was obtained from surveys for LVC patients for 8,246,757 treated eyes. For the LVC patients, it was discovered that the probability of the MRS followed a Rayleigh distribution, with sigma of 3.55 D for myopia and 2.35 for hyperopia and a sub-population ratio of 85% myopia and 15% hyperopia Hence, based on population statistics for approximately 400 million eyes in the national survey and a refractive surgery patient database for approximately 8 million eyes, certain distributions were discovered, which are presented in Table 1.

TABLE 1

| Parameter | Distribution |
| --- | --- |
| Manifest sphere for virgin eyes (General Population) | Normal distribution (see e.g. FIG. 6A) |
| Manifest sphere for refractive surgical candidates (LVC Population) | Rayleigh distribution (see e.g. FIG. 6B) |
| Manifest cylinder (General and LVC Populations) | Normal distribution (see e.g. FIG. 7) |
| Cylinder axis (General and LVC populations) | Uniformly distribution (see e.g. FIG. 13) |
| Keratometry (LVC Population) | Normal distribution (see e.g. FIG. 14) |
| Ocular aberration: high order (LVC Population) | Normal distribution for each Zernike coefficient when the aberrations are expressed in terms of Zernike polynomials |
| Ocular aberration: low order (LVC Population) | Follows the manifest refractions with random deviations |
| Wavefront diameter (LVC Population) | Normal distribution (see e.g. FIG. 15) |

In one example, one million random normal eyes (e.g from a general population random eye model) and one million refractive surgical eyes (e.g. from an LVC population random eye model) were generated based on certain techniques as described herein. Roughly 79% eyes were myopic, 13% were hyperopic and 7% were mixed astigmatic. Such percentages apply to both the general population and the LVC population, and were found to match the data from the population studies, hence providing a realistic distribution.

Hence, the statistics of the simulated eyes followed the statistics assumed for each surgical parameter using the treatment planning mechanisms in a commercial setting. This allowed a "real-world" testing or a "simulated clinical trial" for the development of treatment techniques, or verification and validation of treatment products. It was found that random human eye generation techniques as disclosed herein exhibit the same or similar statistics as historically treated eyes in refractive surgery. Hence, these approaches are effective, accurate, and can improve the speed and efficiency for product development in a commercial environment.

Random eye generation mechanisms according to embodiments of the present invention can be used for any of a variety of purposes. For example, random eye generation mechanisms can be used for verification and validation (V & V) activity to include a large number of eyes at different refractive ranges, which may in some instances be otherwise difficult to achieve. Random eye generation mechanisms can also be used for simulated clinical trials that can test possible ablation characteristics of a particular treatment design or correction modality, for example presbyopia, monovision, and the like. Further, random eye generation mechanisms can be used to refine or develop treatment plans that may require or benefit from a large number of eyes to achieve statistical significance, including instances where a high degree of noise level may otherwise be problematic. According to some embodiments, random eye models can help to counteract such noise, where fluctuations or variations in the data values are averaged out via the use of large number of randomly generated eyes.

In many cases, manifest refraction is an important surgical parameter. In the general population, the myopic and hyperopic patients may typically follow a normal distribution. For refractive surgery candidates, however, a normal distribution may not be appropriate because people having close to emmetropic vision may not need or benefit from surgery. Using certain mathematical models, it can be seen that the Rayleigh distribution may be the most reasonable probability density function, as shown below:

$$f(x; \sigma) = \frac{x}{\sigma^2} e^{-x^2/2\sigma^2} (x \geq 0)$$

Figure 4:
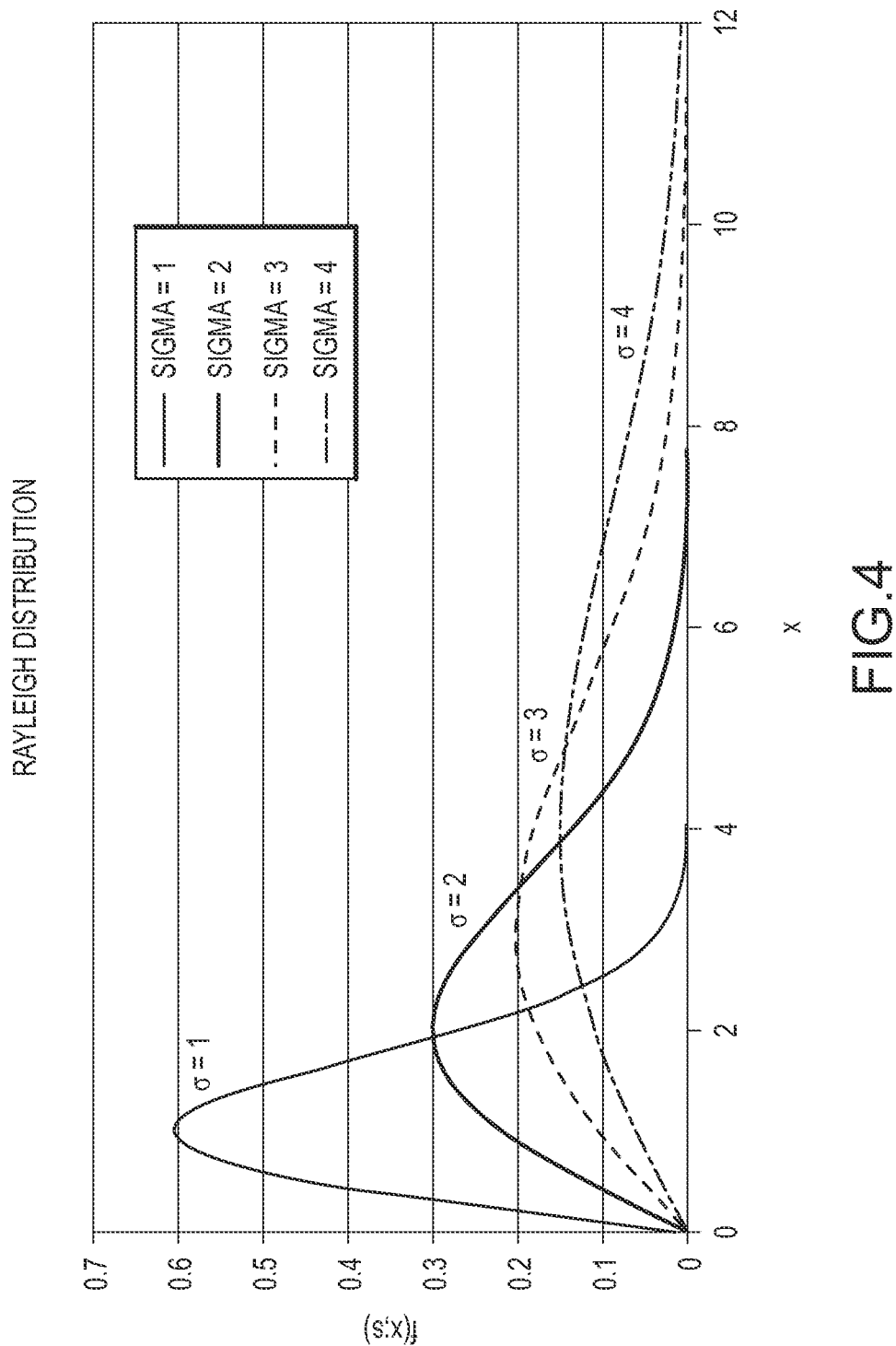
FIG. 4 depicts exemplary Rayleigh distributions according to embodiments of the present invention.

Here, $\sigma$ (or sigma s) is a positive parameter characterizing the mode of the distribution. The x parameter can represent a value over which a Rayleigh distribution is concerned. As further discussed below, illustrative Rayleigh distributions are shown in FIG. 4. For example, with reference to FIG. 6B, with sphere refraction, where x is at zero (0) diopters (D), the probability of a person with such characteristics is zero. When x is at two (2) diopters (D), there is a certain nonzero probability of having a person with such characteristics. When x=sigma, then the probability reaches a peak. For example, where sigma=3.2 diopters, then the probability has a peak at 3.2 diopters. According to some embodiments, the absolute value is used (e.g. probability cannot be negative), for example when referring to myopia.

FIG. 4 shows examples of several Rayleigh (probability) distribution functions. Here, the curves represent certain probability density functions of the Rayleigh distribution. It was found that such distributions are well suited for use in approximating or estimating LVC population parameters. In exemplary embodiments, the integration of each curve from zero to infinity provides a probability sum of one. In this sense, the probability density functions can be considered to be normalized. The curves represent different effects on the range of the distribution and the maximum value of the distribution. For example, where sigma is one, there is a narrower spread in the distribution, with a higher maximum value (e.g. about 0.6). In contrast, where sigma is four, there is a wider spread in the distribution, with a lower maximum value (e.g. about 0.15). As discussed elsewhere herein, whereas FIG. 4 provides a general representation of a Rayleigh distribution, whereas other drawings such as FIG. 6B provide specific representations of Rayleigh distributions that correspond to particular data and/or results (e.g. a sphere power parameter).

Figure 5:
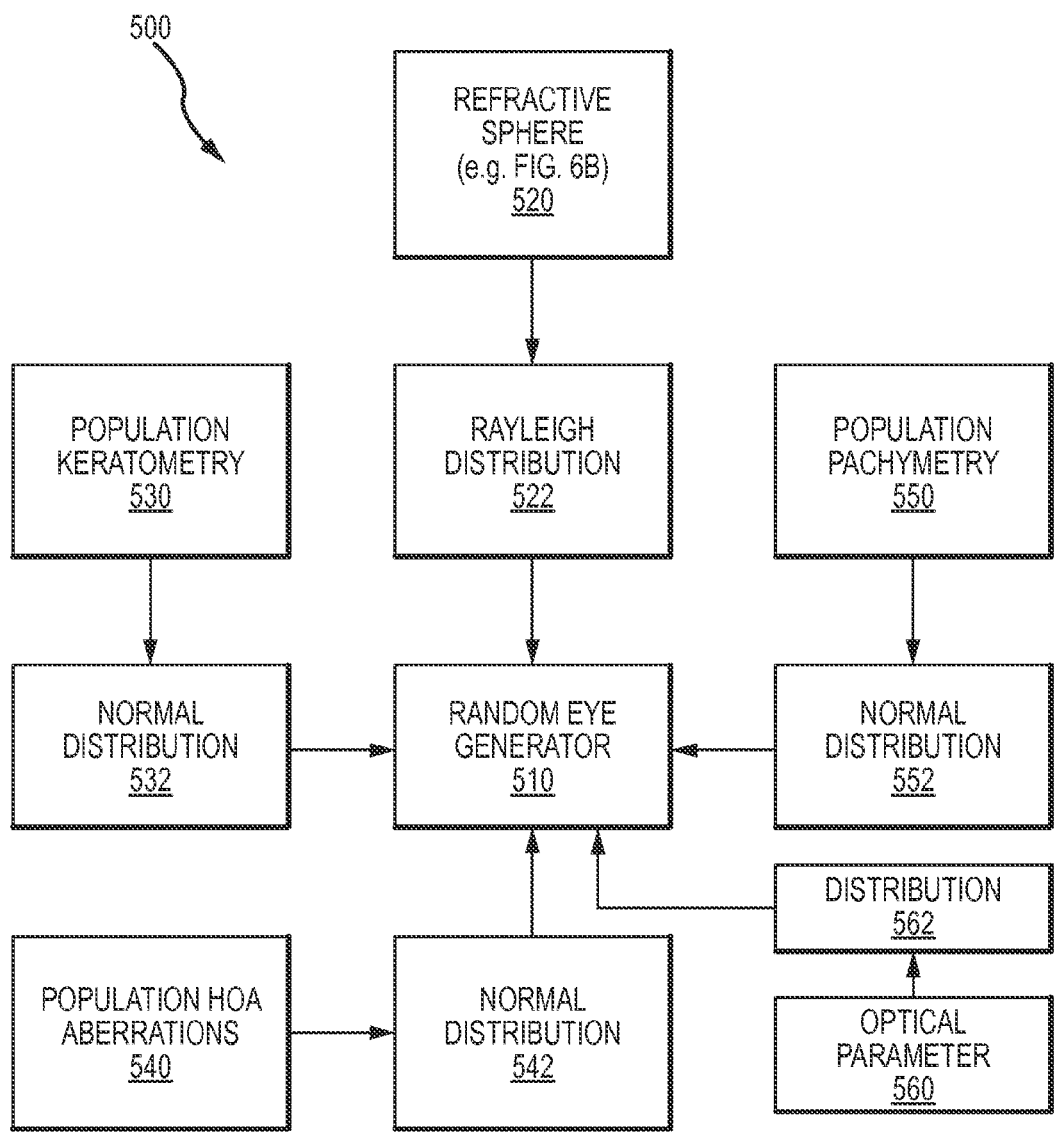
FIG. 5 illustrates aspects of random eye generator systems and methods according to embodiments of the present invention.

FIG. 5 provides a flow chart for the manifest refraction (e.g. population refraction or refractive sphere) and other surgical parameters, including normal refractive surgical parameters and their associated statistical models, for use in developing a random eye generator. A method 500 for determining a random eye generator 510 may include obtaining a set of optical parameters having associated distributions. For example, a first optical parameter can include a refractive sphere parameter 520, a second optical parameter can include a population keratometry parameter 530, a third optical parameter can include a population high order aberration (HOA) parameter 540, and a fourth optical parameter can include a population pachymetry parameter 550. Here, the refractive sphere parameter 520 has a Rayleigh distribution 522 (e.g. Rayleigh distribution for the random values, the population keratometry parameter 530 has a normal distribution 532 of random values, the population high order aberration (HOA) parameter 540 has a normal distribution 542 of random values, and the population pachymetry parameter 550 has a normal distribution 552 of random values. According to some embodiments, a random eye generator 510 can be based on one or more other optical parameters 560 (e.g. cylinder, cylinder axis, wavefront diameter, optical zone, ablation zone, and the like) each having an associated distribution 562.

Figure 8:
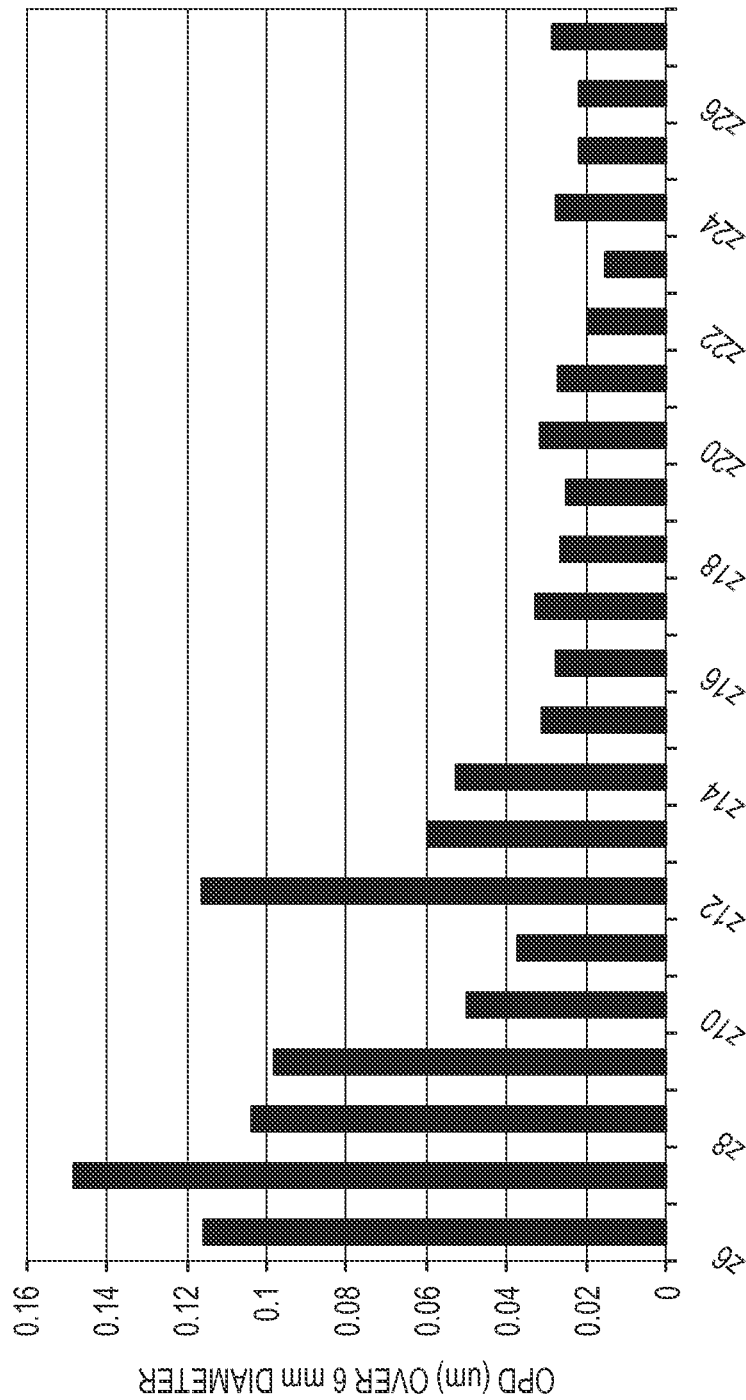
FIG. 8 depicts the magnitude of the standard deviation of Zernike coefficients over a 6 mm diameter, according to embodiments of the present invention.
Figure 16:
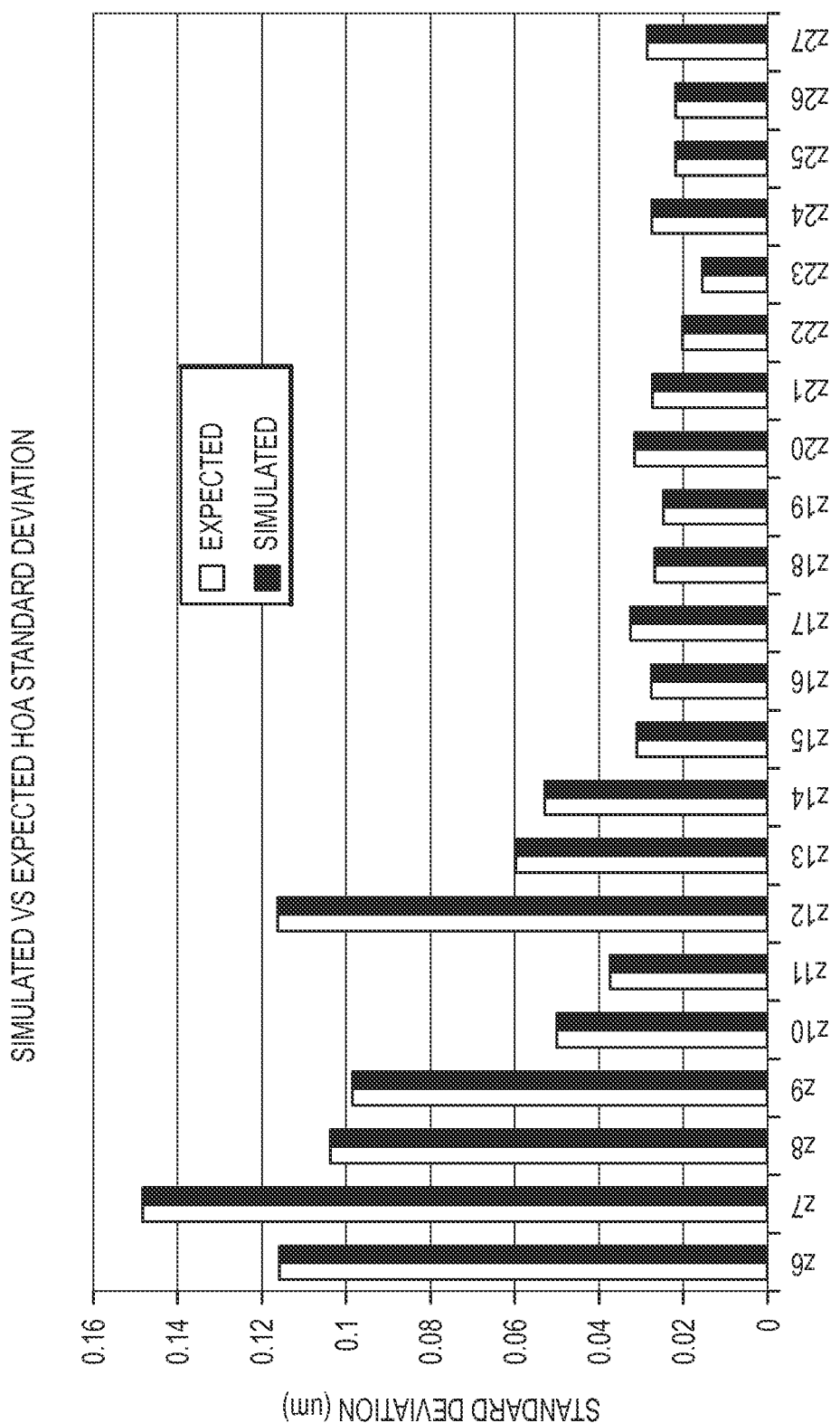
FIG. 16 shows exemplary standard deviation distributions for simulated and expected high order aberration values according to embodiments of the present invention.

According to some embodiments, the refractive sphere may correspond to the manifest sphere for refractive surgical candidates, and may be represented by a Rayleigh distribution. Keratometry and pachymetry population data may each be represented by normal distributions. Similarly, population high order aberration (HOA) data may also be represented by normal distributions. In some instances, HOA aberration data can correspond to Zernike terms of the $6^{th}$ order and higher. In some embodiments, $6^{th}$ order and higher terms can follow a normal distribution, having certain mean and standard deviation values, as depicted in FIGS. 8 and 16. In some instances, the mean may be zero. In some instances, for example in certain primary and secondary spherical aberration features, the mean may be non-zero. Further, population low order aberration (LOA) data may also be implemented. In some cases, LOA data, for example, corresponding to refractive sphere, cylinder, and axis, can be converted into Zernike $3^{rd}$, $4^{th}$, and $5^{th}$ order terms, respectively.

For keratometry, the effect on treatment may be at least one magnitude smaller than the refraction. The values in keratometry may primarily affect the "cosine effect", i.e., the loss of energy due to the curved cornea. According to some embodiments of the present invention, a normal distribution may be assumed, with a mean of 43.5 D and a standard deviation of 1 D for the K1 and K2 values. When a pair of random keratometry values is obtained, the lower number can be assigned K1, and the higher number can be assigned K2. For the K2 axis, again, a uniformly distributed random value between 0 and 180 can be used.

For pachymetry, a normal distribution can be assumed, with a mean of 550 microns and a standard deviation of 25 microns. In some instances, pachymetry data can be used for controlling the eligibility of eyes for treatment. For example, using pachymetry data it may be possible to determine whether the cornea has sufficient thickness to receive a particular refractive treatment. In some instances, the patient cornea may be relatively thin, and the prescribed treatment may involve a relatively deep ablation to correct for a large refractive error. In such cases, the pachymetry data can be used in implementing a safety feature that provides a warning where the residual corneal bed it excessively thin, and thus the treatment is disallowed or prevented.

For high order aberrations, a wavefront can be decomposed into Zernike polynomials. The coefficient of each Zernike polynomial can be considered as normally distributed. In certain embodiments, the means of them may be zero except the primary (c12) and secondary (c24) spherical aberrations (SA). The primary SA may have a mean of 0.08 microns over a 6 mm wavefront diameter and the secondary SA may have a mean of 0.003 microns over a 6 mm wavefront diameter.

For the manifest refraction, a perfect refraction (emmetropia) typically does not require a vision correction. Hence, the embodiment of FIG. 5 may not include a normal distribution of manifest refraction as an input to the random eye generator, but rather describes a Rayleigh distribution (e.g. of random values) for the refractive sphere. As the refraction increases in either the negative or positive direction (although the sign can be ignored and the absolute value considered instead), chances become higher that a vision correction may be needed or desired. At a certain refractive level, the number of eyes available to be treated may reach a maximum or peak. Accordingly, the peak of the Rayleigh curve (e.g. FIG. 6B) can correspond to a most common refractive level. When the refraction passes that level, the number of eyes will decrease due to the lower probability of for higher refractions, i.e., it tends to agree with a normal distribution as the refraction passes over the maximum value of the function.

Figure 5A:
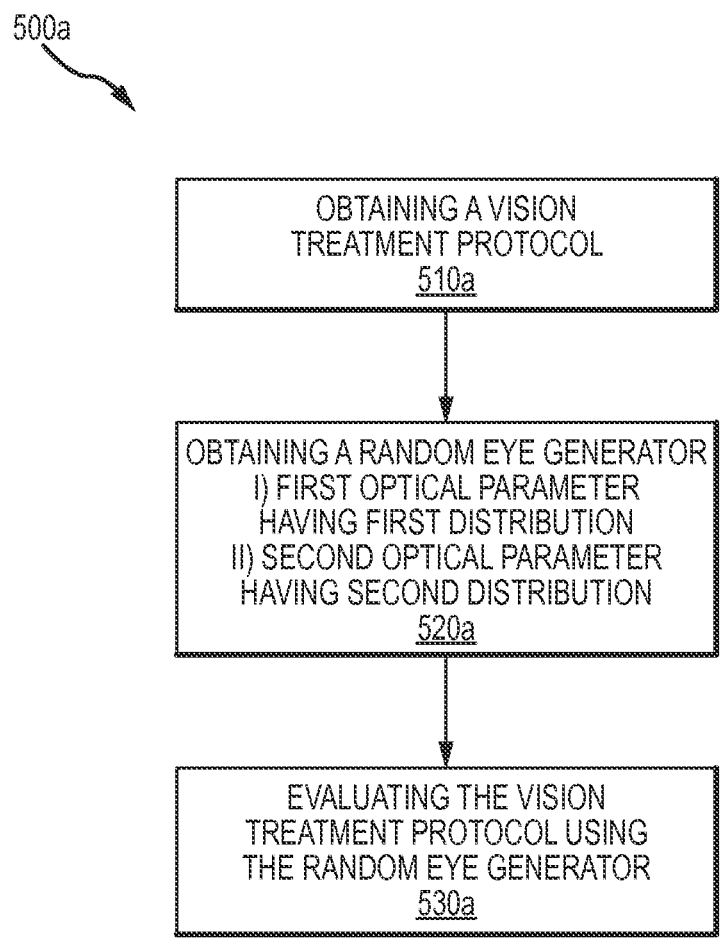
FIG. 5A shows aspects of a process for using a random eye generator to evaluate a vision treatment protocol, according to embodiments of the present invention.

FIG. 5A depicts aspects of a method 500a for evaluating a vision treatment protocol. As shown here, the method includes obtaining a vision treatment protocol as indicated by step 510a, and obtaining a random eye generator as indicated by step 520a. The random eye generator may include any number of optical parameters, as well as distributions associated with the optical parameters. For example, the random eye generator can have a Rayleigh distribution for a manifest sphere power parameter. Further, the method may include evaluating the vision treatment protocol using the random eye generator, as indicated by step 530a.

Figure 5B:
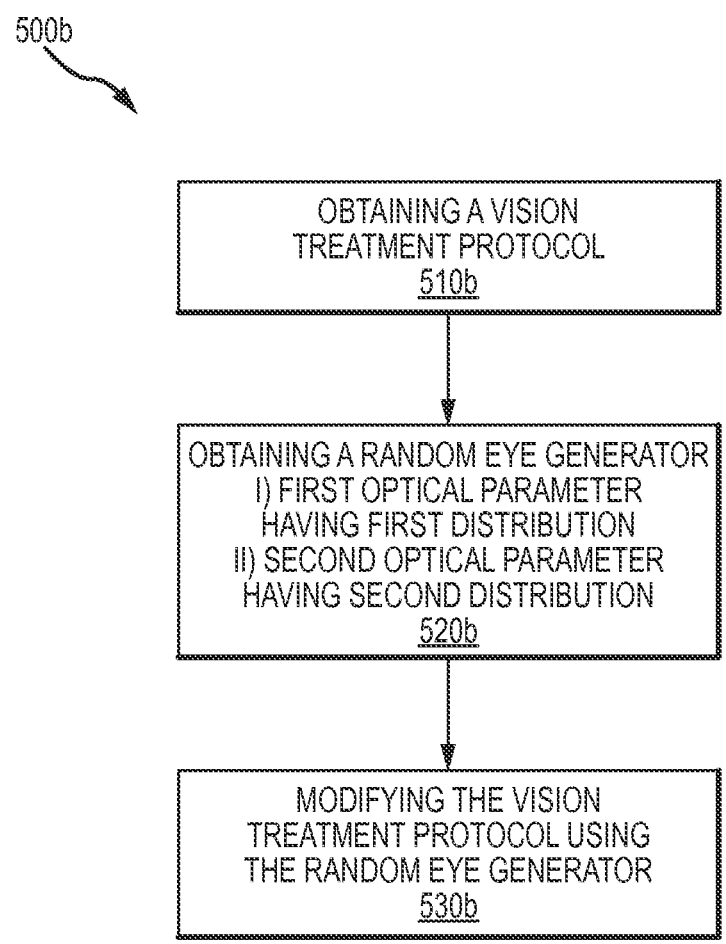
FIG. 5B shows aspects of a process for using a random eye generator to modify a vision treatment protocol, according to embodiments of the present invention.

FIG. 5B depicts aspects of a method 500b for modifying a vision treatment protocol. As shown here, the method includes obtaining a vision treatment protocol as indicated by step 510b, and obtaining a random eye generator as indicated by step 520b. The random eye generator may include any number of optical parameters, as well as distributions associated with the optical parameters. For example, the random eye generator can have a Rayleigh distribution for a manifest sphere power parameter. Further, the method may include modifying the vision treatment protocol using the random eye generator, as indicated by step 530b.

Figure 6A:
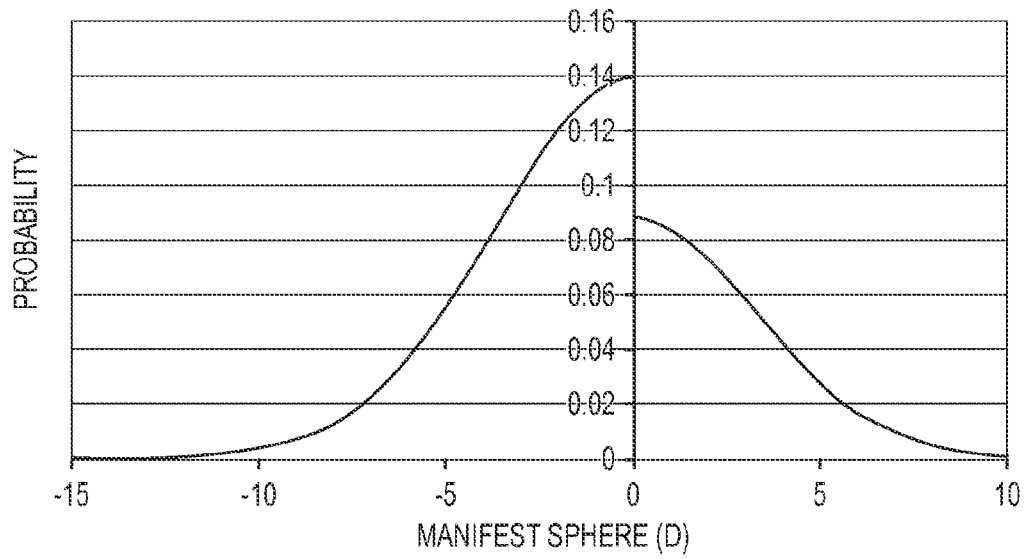
FIGS. 6A and 6B depict exemplary distributions for general population data and LVC candidate data according to embodiments of the present invention.
Figure 6B:
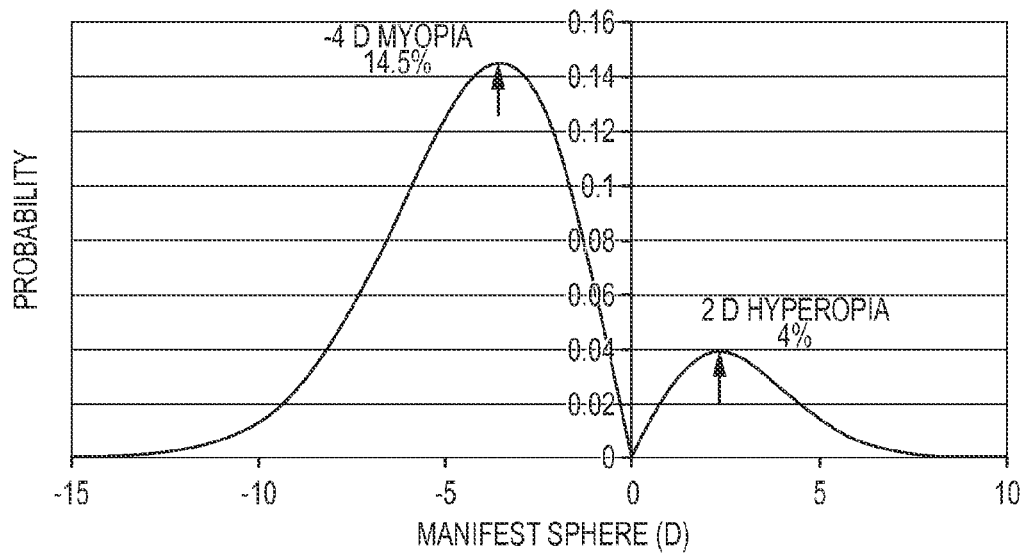

Probability functions (MRS curves) for the manifest sphere for the general population are shown in FIG. 6A, and for LVC candidates are shown in FIG. 6B. Hence, as depicted in FIG. 6A, the general population results were found to be suitably represented by a normal distribution. As depicted in FIG. 6B, the LVC population results (refractive sphere) were found to be suitably represented by a Rayleigh distribution. Here, the refraction is about zero, the manifest sphere is also about zero. Further, where the manifest sphere is about −4 (e.g. myopia), the probability is at a maximum of about 14.5%, and where the manifest sphere is about 2.5 (e.g. hyperopia), the probability is at a maximum of about 4%. It is at these values where the highest proportion of the population is seeking laser vision correction or vision treatment. These results correspond to data obtained from certain surveys as discussed elsewhere herein.

For low order aberrations such as sphere power, the values for a population of individuals that may or may not have vision problems follow a normal distribution as shown in FIG. 6A. And as shown in FIG. 6B, the sphere power for a population of LASIK candidates can follow a Rayleigh distribution. As discussed elsewhere herein, for both populations (i.e. general population and LASIK population), the values for other optical parameters such as cylinder power, cylinder axis, wavefront diameter, and high order aberrations, it is possible to assume a normal distribution for any of these parameters.

Figure 7:
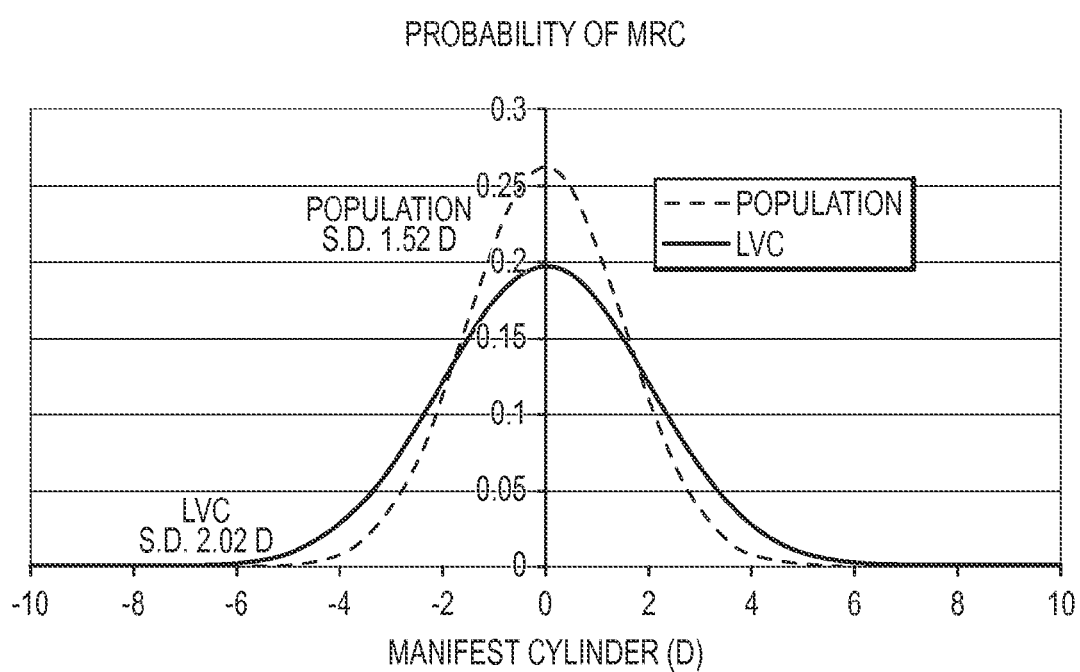
FIG. 7 shows exemplary distributions for general population data and LVC candidate data according to embodiments of the present invention.

FIG. 7 depicts probability functions (MRC curve) for the manifest cylinder for the general population and for LVC candidates. For the cylinder axis, a uniformly distributed random value between 0 and 180 was used. Here, the mean value corresponds to the highest probability of occurrence of a particular manifest cylinder value, e.g. zero diopters. For manifest refractive cylinder (MRC), a normal distribution was found to provide an appropriate match, with the standard deviation of 1.52 D for the population and 2.02 D for the LVC candidates. Hence, it can be seen that the data for the general population tends to be closer to the mean or expected value, whereas the data for the LVC candidates tends to be more spread out. It can be seen that healthy eyes tend to have very little or no cylinder and LVC eyes have higher cylinder. Therefore, the spread is be wider with LVC eyes.

FIG. 8 shows the magnitude of the standard deviation of Zernike coefficients over a 6 mm diameter, according to embodiments of the present invention. Here, the standard deviation in optical path difference (OPD) is presented in microns over a 6 mm wavefront diameter for high order Zernike coefficients. These results were obtained from a data set that includes thousands of eyes, and is different from the general population and LVC data sets discussed elsewhere herein. This data set was used to calculate the mean and standard deviation of Zernike coefficients for thousands of eyes. The data presented in FIG. 8 corresponds to high order Zernike terms of the $6^{th}$ order and higher. For individual terms, it can be seen that the terms have a particular variation, and there is variation from term to term. According to some embodiments, results from this data set were used to develop random eye generators. According to some embodiments, the mean values are zero except for primary (Z12) and secondary (Z24) spherical aberrations where the mean values are nonzero. In some embodiments, the mean for the primary spherical aberration (SA, Z12) is 0.08 microns over a 6 mm diameter, and the mean for the secondary SA (Z24) is 0.003 microns for a 6 mm diameter.

For low order aberrations, the manifest refraction can be used, adjusted by a random deviation. For example, the random deviation can be normally distributed with zero mean and a standard deviation of 0.25 D for sphere, 0.125 D for cylinder, and 5 degrees for the cylinder axis. This can result in the formation of a wavefront refraction. These randomly generated refractions can then be converted to Zernike coefficients, as described in G.-m. Dai, Wavefront Optics for Vision Correction, SPIE Press (2008), incorporated herein by reference. In some instances, the refractions can be converted to Zernike coefficients over a 6 mm wavefront diameter, or another wavefront diameter value.

According to some embodiments, when a wavefront diameter is not 6 mm, the random Zernike coefficients can be rescaled to a necessary or desired diameter (whether it is larger or smaller) via a Zernike rescaling algorithm, such as those described in U.S. Pat. Nos. 7,717,562 and 7,887,187, the contents of which are incorporated herein by reference.

In certain embodiments, for the random generation of a wavefront diameter, a normal distribution can be assumed. The mean for the wavefront diameter may be 5.5 mm and the standard deviation may be 1 mm.

In certain embodiments, for the optical zone (OZ) and ablation zone (AZ), it can be generally selected based on the desired use. For a verification and validation (V & V) application, it may be desirable to use a randomly generated set of OZ and AZ to test various combinations of OZ and AZ, for example that may be allowed by the software.

Once the random eyes are generated, the associated surgical parameters can be used to calculate treatment targets as well as the treatment tables. Often, the treatment tables are laser instructions that are used by the surgeons. Exemplary aspects of treatment target and treatment table techniques are discussed in U.S. patent application Ser. No. 14/073,583 filed Nov. 6, 2013, which is incorporated herein by reference.

Figure 9:
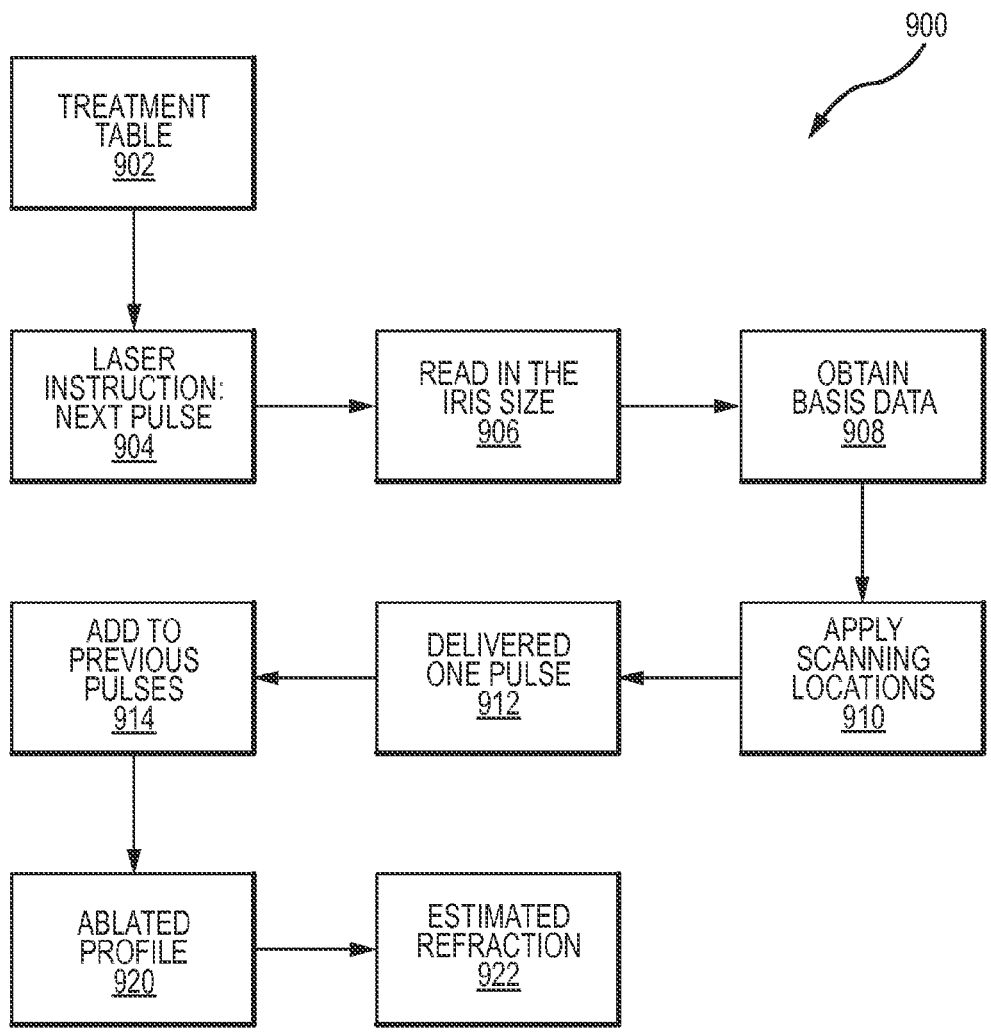
FIG. 9 illustrates aspects of systems and methods for determining ablation profiles and estimated refractions, according to embodiments of the present invention.

FIG. 9 depicts an exemplary process 900 for a virtual ablation treatment table. This process can be used to simulate a laser ablation. Typically, treatment processing systems operate based on input parameters such as refractive error data, optical zone data, transition zone data, keratometry data, pachymetry data, high order aberration data, and the like. In actual surgical procedures (non-simulated), such parameters can be based on data obtained from an actual patient. According to embodiments of the present invention, random eye generators can be used to provide such input parameters when evaluating or simulating certain treatment modalities. According to some embodiments, FIG. 9 depicts a deterministic process.

As shown here, the process of assembling a set of laser pulses into a cumulative ablated profile or ablation volume, and then translating that profile or volume to an estimated refraction, can involve a number of steps. The process can involve a treatment table 902 (e.g. a file containing lines of information for instructing the laser to perform certain operations) which is read and then executed so as to produce the ablated profile or target shape 920. For example, the treatment table 902 can be used to generate a laser pulse instruction 904. An iris size 906 can also be incorporated, and basis data 908 can be obtained based on the iris size. In some instances, techniques may involve the use of x,y positioning factors 910. For example, embodiments encompass techniques which account for effects related to decentering or x,y scanning locations 910 of the pulse beam. Individual pulses 912 can be added to previous pulses 914, so as to provide the ablated profile 920. An estimated refraction 922 can be determined based on the ablated profile 920. According to some embodiments, the estimated refraction 922 can be based on the simulated ablation profile by decomposing the profile surface into Zernike polynomials to obtain the refraction.

Figure 10:
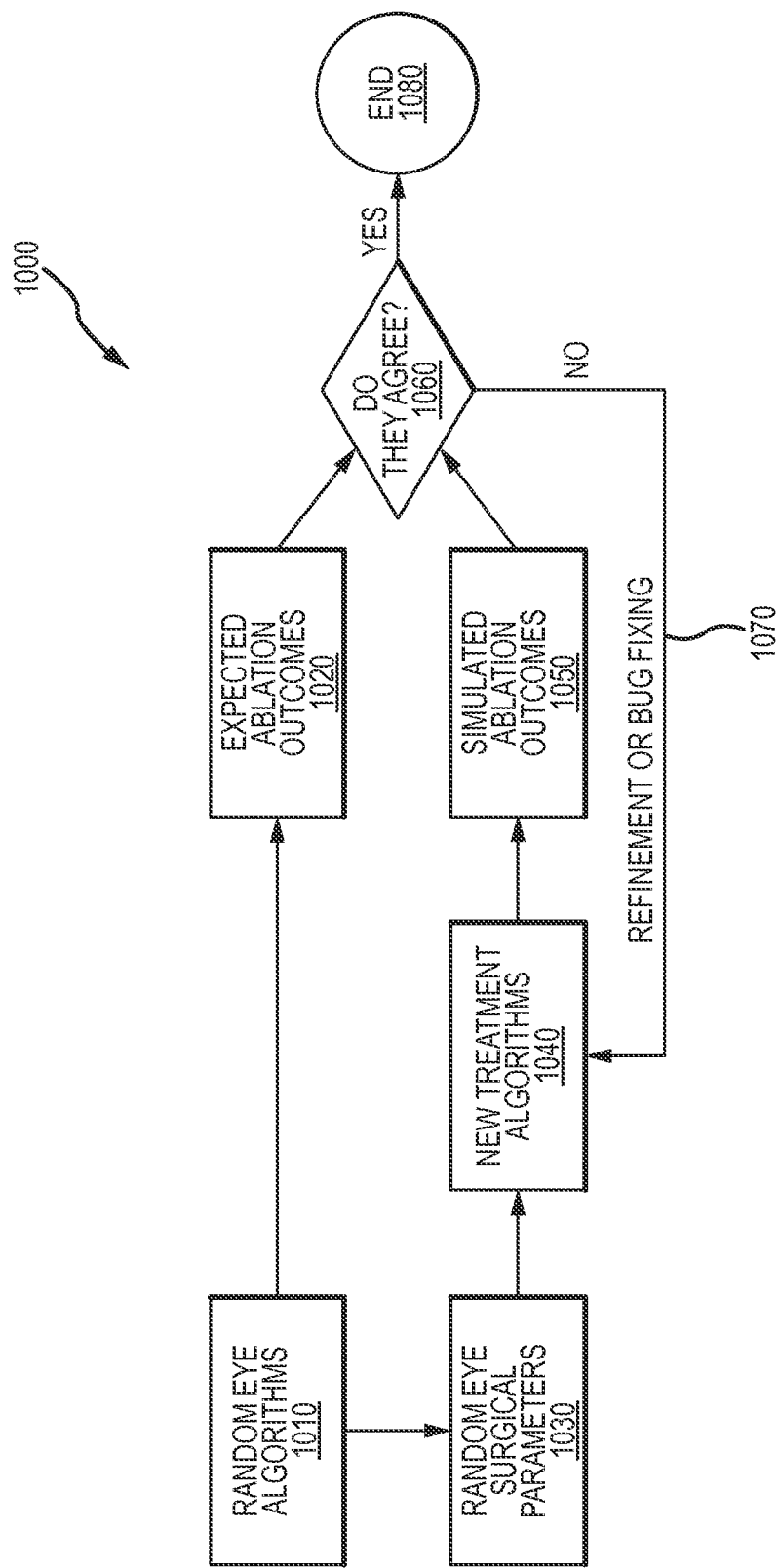
FIG. 10 depicts aspects of systems and methods for evaluating and/or adjusting treatment protocols or algorithms, according to embodiments of the present invention.

FIG. 10 depicts aspects of refinement or bug fixing for random eye generation systems and methods. According to some embodiments, random eye generation techniques can be used to refine or to fix bugs in treatment software or systems. Random eye generation techniques can also be used for purposes of verification and validation (V & V). In some instances, the generated random eyes as well as the associated surgical parameters can be used to test treatment algorithms or techniques. If the tested techniques do not sufficiently agree with the expected outcome, a refinement can be implemented or bugs can be fixed. In some instances, a new treatment algorithm may correspond to a target controller module as discussed elsewhere herein. In some instances, a simulated ablation outcome may correspond to a virtual ablation module as discussed elsewhere herein.

As depicted here, a refinement or bug fixing process 1000 may include providing a random eye generator 1010 that involves a set of optical parameters with corresponding value distributions. Expected or ideal ablation outcomes 1020 (e.g. theoretical optical surface or shape) can be determined based on the random eye generator 1010. Also, random eye surgical parameters 1030 can be determined based on the random eye generator 1010, and a treatment algorithm 1040 can be used to develop simulated ablation outcomes 1050 (e.g. optical surface or shape). The expected ablation outcome 1020 and the simulated ablation outcome 1050 can be compared at step 1060, and if a difference between the expected ablation outcome 1020 and the simulated ablation outcome 1050 meets a certain tolerance, the treatment algorithm 1040 can be authorized with a pass as indicated as step 1080. If, however, the comparison step 1060 indicates that the difference between the expected ablation outcome 1020 and the simulated ablation outcome 1050 does not meet a certain tolerance, then the treatment algorithm can be refined or a bug can be fixed as indicated by step 1070 so as to obtain an updated treatment algorithm which can then be evaluated.

Figure 10A:
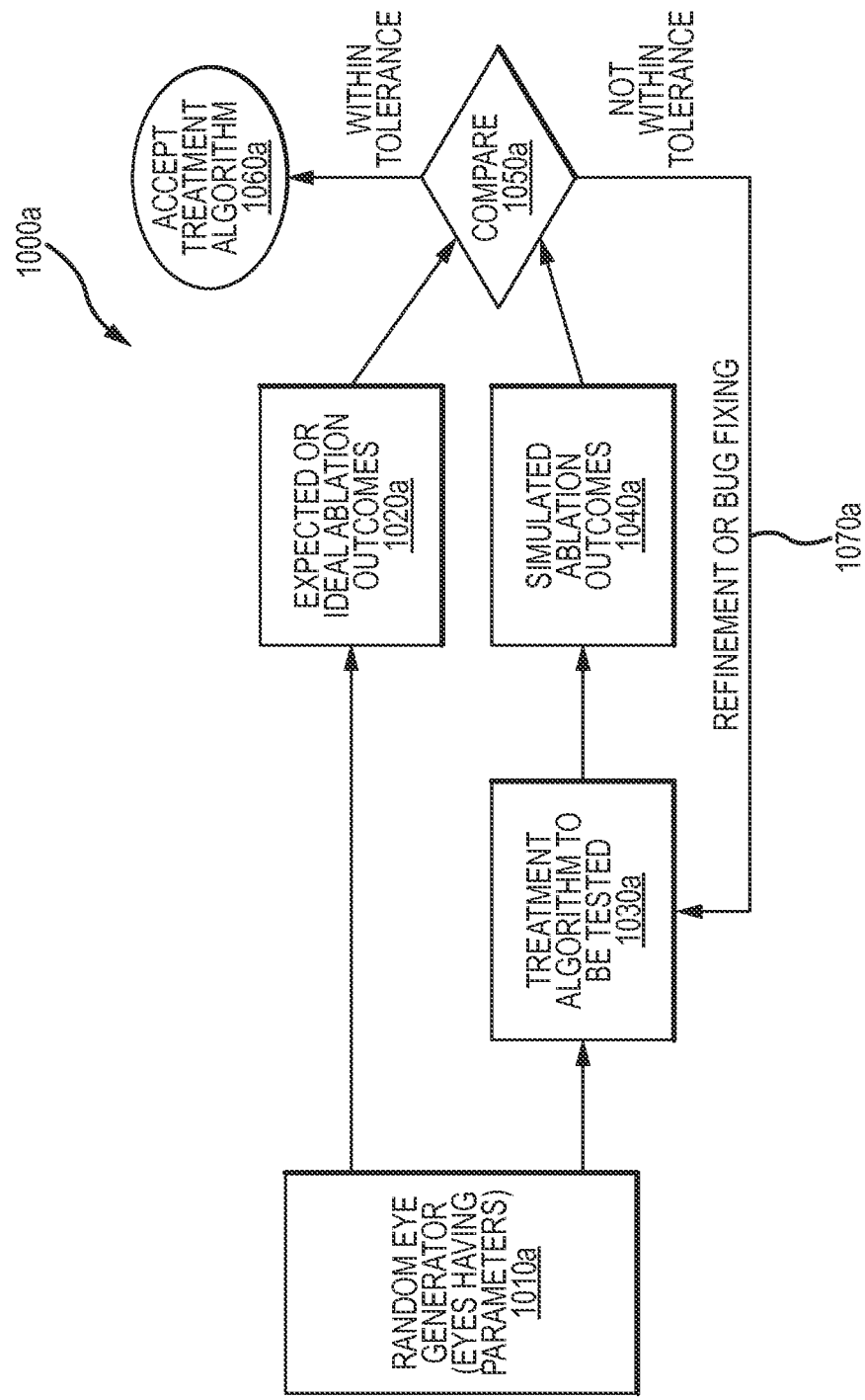
FIG. 10A depicts aspects of systems and methods for evaluating and/or adjusting treatment protocols or algorithms, according to embodiments of the present invention.

FIG. 10A depicts aspects of refinement or bug fixing for random eye generation systems and methods, according to embodiments of the present invention. As shown here, a method 1000a may involve developing a number of eyes based on a random eye generator 1010a, wherein individual eyes so obtained have certain optical parameters with associated value distributions. For example, the random eye generator can generate a set of 2000 eyes, where individual eyes have optical parameters (such as manifest sphere power) presenting an associated value distribution (such as a Rayleigh distribution). The distribution can represent a statistical distribution function, and a random number generator can be used to generate optical parameter values that fall randomly within the distribution. Hence, a histogram or occurrence plot of different values within the distribution curve will correspond to the probability distribution function, coinciding with the probability of a certain value occurring within the distribution range. The expected or ideal ablation outcomes 1020a can be produced using the random eye generator 1010a and the set of eyes generated by the generator. Relatedly, the ideal ablation outcomes 1040a can be produced using the random eye generator 1010a and the set of eyes generated by the generator, as processed by the treatment algorithm 1030a. In use, any of a variety of treatment algorithms or techniques 1030a can be evaluated by this method. For example, treatments involving Variable Spot Scanning (VSS) or VSS Refractive™ technology, which refers to an excimer laser technique for scanning beams at variable pulse diameters at different locations (e.g. x,y position) over an entire treatment area, can be evaluated. Similarly, deconvolution treatment techniques such as those described in US patent application Ser. No. 14/044,650 filed Oct. 2, 2013 can be evaluated. Likewise, any of a variety of wavefront, wavefront-guided, and/or topography assisted treatments can be evaluated. According to some embodiments, the techniques depicted in FIGS. 10 and 10A can be used to validate software products by using a random eye generator.

As indicated by step 1050a, the expected ablation outcomes 1020a can be compared with the simulated ablation outcomes 1040a. In some cases, the comparison 1050a can be made on an eye-to-eye basis, or a surface-to-surface basis. In some cases, individual components of the ablation outcomes can be compared in the comparison step 1060, for example similar to the comparisons shown in FIGS. 11, 12, 14, 15, and 16. The comparison 1050a can be used to determine whether a difference between an expected ablation outcome 1020a and a simulated ablation outcome 1040a is within a certain tolerance (e.g. the expected and simulated outcomes are sufficiently close). If the difference is within a tolerance, the method may include accepting or authorizing the treatment algorithm, as indicated by step 1060a. In this sense, the method may involve a verification of the treatment algorithm. If the difference is not within a tolerance (e.g. the expected and simulated outcomes are not sufficiently close), the method may include refining the treatment or fixing a bug in the treatment, as indicated by step 1070a. Hence, the method 1000a can be implemented as a way to provide a simulated clinical trial involving the treatment algorithm, and can be performed using any number of generated eyes.

As an example, for the purpose of treatment validation, one million random eyes were generated as LASIK surgery candidates. Exemplary treatment validation techniques are discussed in U.S. Patent Application No. 61/901,216 filed Nov. 7, 2013, the content of which is incorporated herein by reference. The statistical parameters for manifest sphere, cylinder, cylinder axis, keratometry, keratometric axis, wavefront diameter, and high order aberrations were used during the generation of the random eyes. Exemplary distributions are depicted in FIGS. 11 to 16. The information provided in FIGS. 11 to 16 can be used to illustrate how a random eye generator is validated. Put another way, it is possible to ensure that the random eye generator is working appropriately based on information such as that shown in FIGS. 11 to 16. Once the random eye generator is validated, then it can be implemented into a V&V (verification and validation) process for treatment software.

Figure 11:
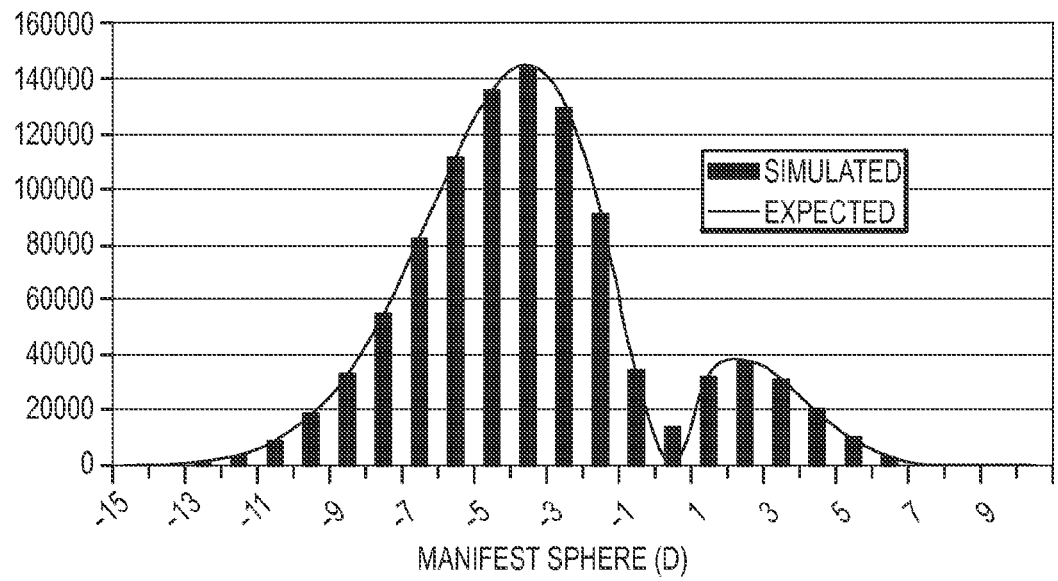
FIG. 11 shows exemplary distributions for simulated and expected manifest sphere values according to embodiments of the present invention.

FIG. 11 shows a histogram of the simulated manifest sphere as it compared to the expected values from the Rayleigh distribution. A near perfect-fit except at zero refraction was observed.

Figure 12:
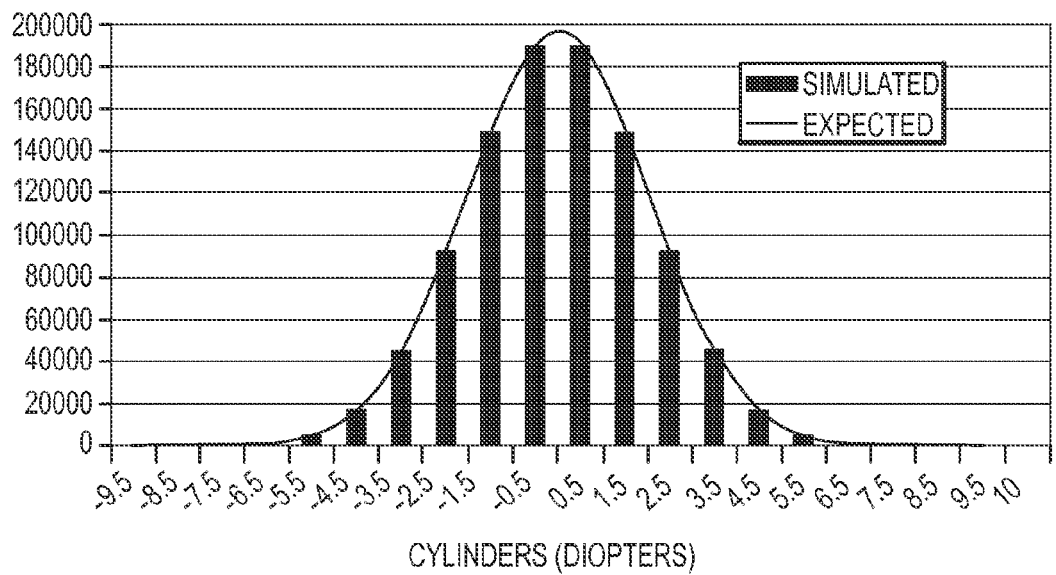
FIG. 12 shows exemplary distributions for simulated and expected manifest cylinder values according to embodiments of the present invention.
Figure 13:
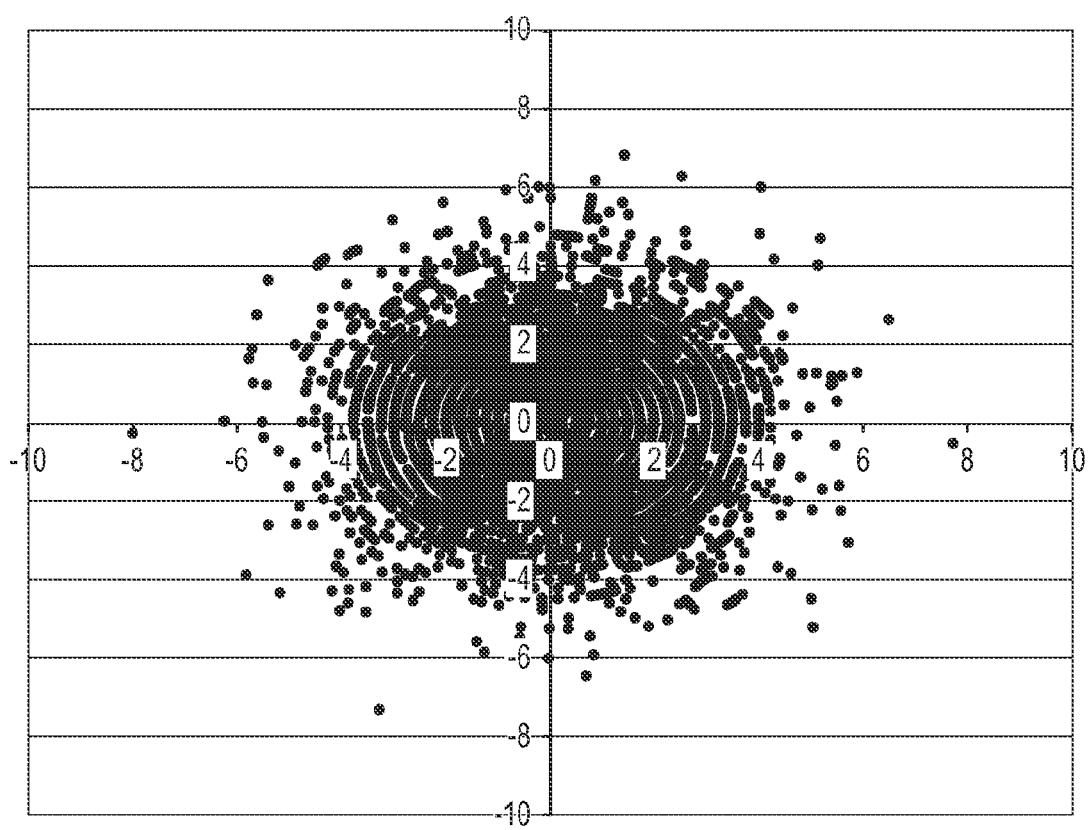
FIG. 13 shows an exemplary vector plot distribution for simulated cylinder axis values according to embodiments of the present invention.

FIG. 12 shows a histogram of the simulated manifest cylinder as it compared to the expected values from the normal distribution. FIG. 13 shows a two-dimensional scatter plot for the simulated manifest cylinder vector. Hence, for the manifest cylinder, the histogram of the simulated cylinder magnitude is shown in FIG. 12 as it is compared to the expected values in the normal distribution, and the vector form is shown in FIG. 13. As shown in this vector plot for cylinder axis, there is a uniform distribution, where the rings correspond to 0.25 Diopter increments. According to some embodiments, the uniform distribution can be characterized as discrete in the radial direction (e.g. a discrete assumption of 0.25 D increments for the cylinder power, such as 2.25 D, 3.75 D, and the like). According to some embodiments, the uniform distribution can be characterized as continuous from the tangential direction because the axis is uniformly distributed. In some instances, this simulation may be considered in a manner similar to a phoropter, having a set size of 0.25 Diopters. Here, due to the uniform distribution, is can be seen that each value may have an approximately equal probability of occurrence. According to some embodiments, axis values can be provided in a uniform distribution. Hence, there is an equal probability that values may have the same value within a range. For example, with regard to cylinder axis, it is possible to say the axis is uniformly distributed between 0 and 180. Put another way, any value between 0 and 180 has the same probability of occurring. This is in contrast to a normal distribution (e.g. bell curve) where the probability of occurring closer to the mean value is higher, and the probability of occurring further away from the mean value is lower.

Figure 14:
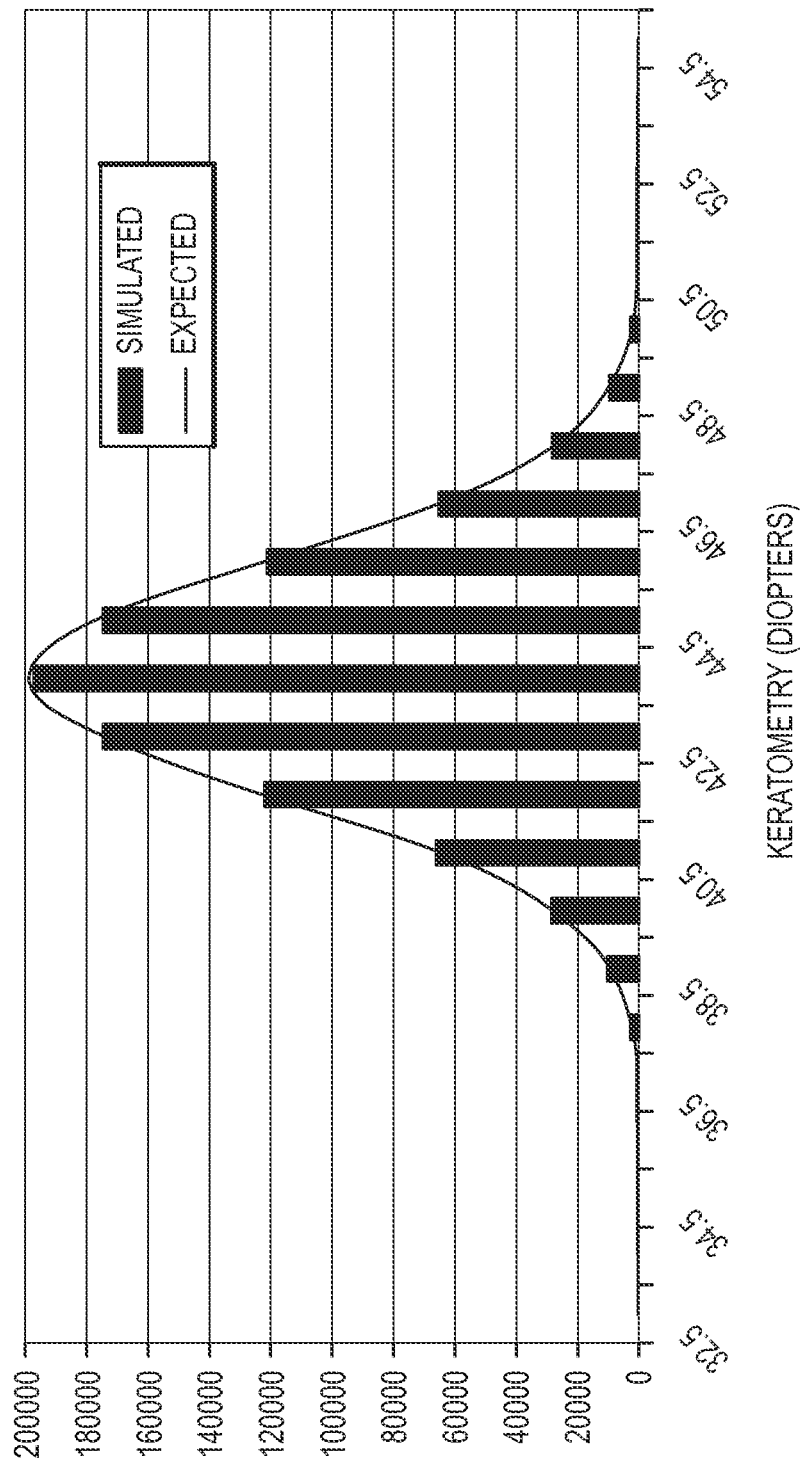
FIG. 14 shows exemplary distributions for simulated and expected keratometry values according to embodiments of the present invention.

FIG. 14 depicts a histogram of the keratometry (K1) as it is compared to the expected values from the normal distribution. In certain embodiments, the keratometry, the K1 value is simulated as a normal distribution with a mean of 43.5 D and a standard deviation of 2 D, such as for the result is shown in FIG. 14. For K2, it can be considered by factor in the K1 value as well as the cylinder value for the particular eye. A normally distributed random number with zero mean and unity standard deviation is added to obtain the random nature of the K2 value. Typically, cylinder may originate from the corneal, and some amount of cylinder may originate from the lens. It is possible to calculate one K value based on the other K value and the cylinder value or power.

Typically, the K1 and K2 keratometry values are associated with orthogonal powers or curvatures of the cornea, and can be used in developing aspects of refractive surgery, contact lenses, and other vision treatment modalities. For example, the K1 and K2 values can be used when developing a curvature for a posterior side of a contact lens, so that the lens can rest with a good fit on the surface of the eye. Further, the K1 and K2 values can be used in refractive surgery modalities to implement a cosine effect, so as to compensate for the curved surface of the cornea when delivering ablation pulses thereto. What is more, the K1 and K2 values can be used in treatment to implement wavefront propagation techniques. For example, a wavefront data can be obtained corresponding to the pupil plane, which may be approximately 3.5 mm from the corneal surface. Such data can be transformed via wavefront propagation techniques (e.g. from the pupil plane to the corneal plane or surface) so that an ablation pattern can be developed from the cornea.

Once the statistics for each desired parameter are obtained, it is possible to randomly generate any number of eyes. For the wavefront aberrations, the low order wavefront aberration can be simulated from the manifest refraction. The wavefront sphere can be simulated from the manifest sphere plus a normally distributed random number with zero mean and a standard deviation of 0.25 D. Similarly, the wavefront cylinder can be simulated from the manifest cylinder plus a normally distributed random number with zero mean and a standard deviation of 0.125 D. Finally, the cylinder axis can be simulated from the manifest cylinder axis plus a normally distributed random number with zero mean and a standard deviation of 5 degrees. If the axis is greater than 180 degree or smaller than 0, it can be rounded over. For example, 184-degrees can become 4-degrees, and −3 degrees can become 177 degrees. Once the wavefront sphere, cylinder, and cylinder axis are obtained, the corresponding Zernike coefficients z3, z4, and z5 can be calculated for a wavefront diameter of 6 mm. Aspects of this process are discussed in G.-m. Dai, Wavefront Optics for Vision Correction (SPIE Press, 2008), incorporated herein by reference.

Further, it is possible to simulate the high order aberrations, with each term having a zero mean and a given standard deviation for normally distributed random numbers. For the primary and secondary spherical aberration terms, however, the means may not be zero. Once the high order aberrations are obtained, they can be combined to the total wavefront aberration for a 6 mm diameter. Table 2 below depicts low order and high order aberration information, corresponding to Zernike polynomials up to the fourth order.

TABLE 2

| i | n | m | Zernike polynomials | Name |
|---|---|---|---|---|
| 0 | 0 | 0 | 1 | piston |
| 1 | 1 | −1 | $2\rho \sin \theta$ | y-tilt |
| 2 | 1 | 1 | $2\rho \cos \theta$ | x-tilt |
| 3 | 2 | −2 | $\sqrt{6}\rho^2 \sin 2\theta$ | y-astigmatism |
| 4 | 2 | 0 | $\sqrt{3}(2\rho^2 - 1)$ | defocus |
| 5 | 2 | 2 | $\sqrt{6}\rho^2 \cos 2\theta$ | x-astigmatism |
| 6 | 3 | −3 | $\sqrt{8}\rho^3 \sin 3\theta$ | y-trefoil |
| 7 | 3 | −1 | $\sqrt{8}(3\rho^3 - 2\rho) \sin \theta$ | y-coma |
| 8 | 3 | 1 | $\sqrt{8}(3\rho^3 - 2\rho) \cos \theta$ | x-coma |
| 9 | 3 | 3 | $\sqrt{8}\rho^3 \cos 3\theta$ | x-trefoil |
| 10 | 4 | −4 | $\sqrt{10}\rho^4 \sin 4\theta$ | y-quadrafoil |
| 11 | 4 | −2 | $\sqrt{10}(4\rho^4 - 3\rho^2) \sin 2\theta$ | y-secondary astigmatism |
| 12 | 4 | 0 | $\sqrt{5}(6\rho^4 - 6\rho^2 + 1)$ | spherical aberration |
| 13 | 4 | 2 | $\sqrt{10}(4\rho^4 - 3\rho^2) \cos 2\theta$ | x-secondary astigmatism |
| 14 | 4 | 4 | $\sqrt{10}\rho^4 \cos 4\theta$ | x-quadrafoil |

As shown here, low order aberrations correspond to those polynomials where n≤2 (i=$Z_{0-5}$), and high order aberrations correspond to those polynomials where n≥3 (i=$Z_{6-12}$). As shown here, high order polynomials include third order (n=3) and fourth order (n=4) aberrations. Generally, high order aberrations include third order errors and above.

Figure 15:
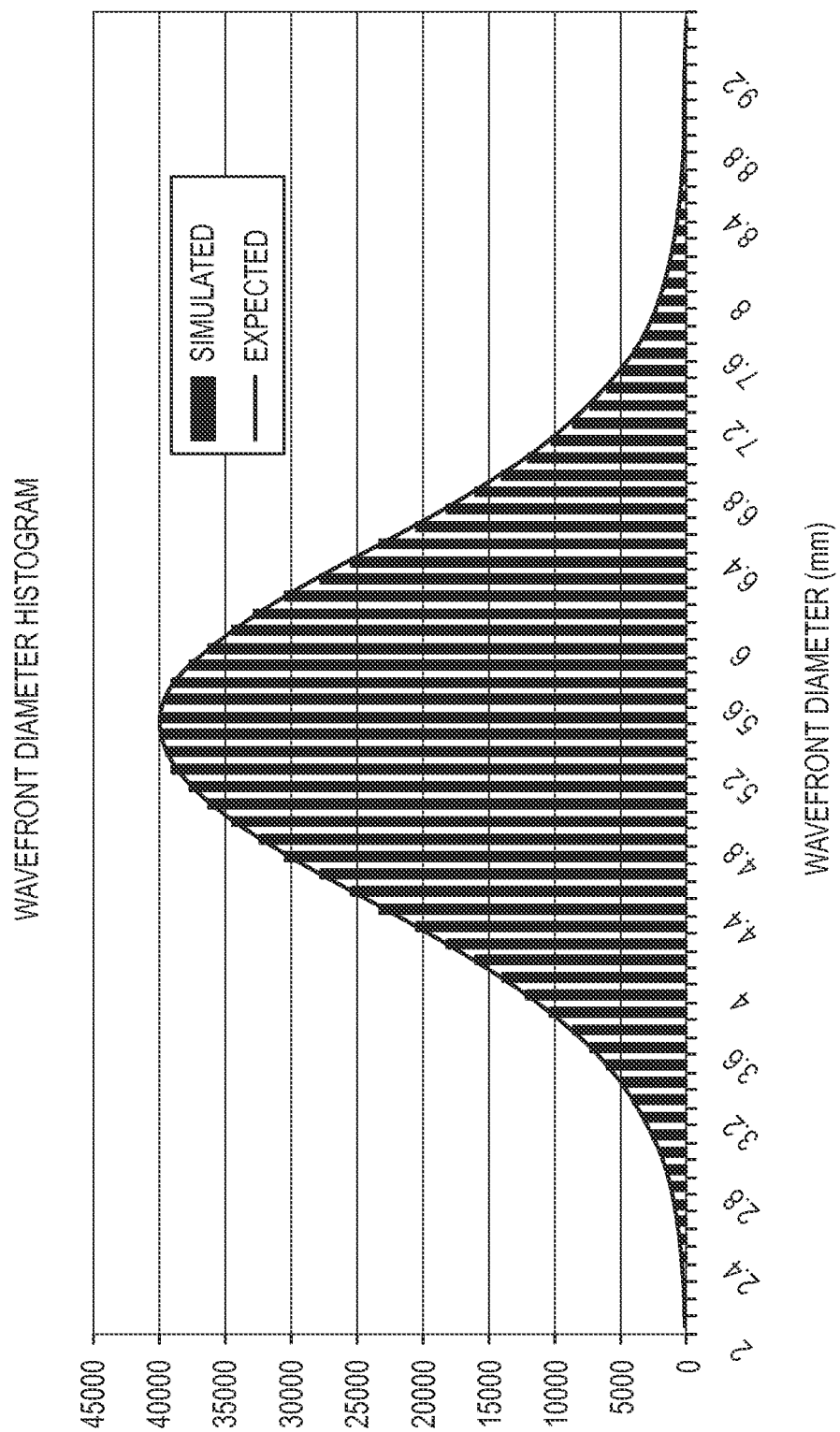
FIG. 15 shows exemplary distributions for simulated and expected wavefront diameter values according to embodiments of the present invention.

Still further, a random wavefront diameter can be generated, with a mean of 5.5 mm and a standard deviation of 1 mm. FIG. 15 shows a histogram for the wavefront diameter as it compared to the expected values. In certain embodiments, wavefront diameter values can be simulated as a normal. Once the wavefront diameter is obtained, the wavefront can be scaled from 6 mm to the given size, with the calculated of new set of Zernike coefficients, as given by G.-m. Dai, Wavefront Optics for Vision Correction (SPIE Press, 2008). The statistics (standard deviation) of the high order aberrations of the 1,000,000 wavefront is shown in FIG. 16, which depicts the standard deviation of the high order Zernike terms as they compared to the expected values. According to some embodiments, the mean values are zero except for primary (Z12) and secondary (Z24) spherical aberrations where the mean values are nonzero. In some cases, the mean value for the primary spherical aberration (SA, Z12) is 0.08 microns over a 6 mm diameter. In some cases, the mean value for the secondary SA (Z24) is 0.003 microns for a 6 mm diameter. In some cases, the mean values for all Zernike coefficients are zero except for primary SA and secondary SA where the mean values are 0.08 and 0.003 um, respectively, over a 6 mm diameter.

From these one million simulated eyes, it was observed that 79.44% were myopic, 13.17% were hyperopic, and 7.38% were mixed astigmatic eyes. This is a very reasonable distribution for LASIK candidates. In addition, for the manifest sphere, 85.14% were myopic and 14.86% were hyperopic. They also compared very well to the expected values of 85% and 15%, respectively.

All patent filings (including patents, patent applications, and patent publications), scientific journals, books, treatises, technical references, and other publications and materials discussed in this application are incorporated herein by reference in their entirety for all purposes.

A variety of modifications are possible within the scope of the present invention. A variety of parameters, variables, factors, and the like can be incorporated into the exemplary method steps or system modules. While the specific embodiments have been described in some detail, by way of example and for clarity of understanding, a variety of adaptations, changes, and modifications will be obvious to those of skill in the art. Although the invention has been described with specific reference to a wavefront system using lenslets, other suitable wavefront systems that measure angles of light passing through the eye may be employed. For example, systems using the principles of ray tracing aberrometry, tscherning aberrometry, and dynamic skiascopy may be used with embodiments of the current invention. The above systems are available from TRACEY Technologies of Bellaire, Tex., Wavelight of Erlangen, Germany, and Nidek, Inc. of Fremont, Calif., respectively. Embodiments of the invention may also be practiced with a spatially resolved refractometer as described in U.S. Pat. Nos. 6,099,125; 6,000,800; and 5,258,791, the full disclosures of which are incorporated herein by reference. Treatments that may benefit from the invention include intraocular lenses, contact lenses, spectacles and other surgical methods in addition to refractive laser corneal surgery.

Each of the calculations or operations discussed herein may be performed using a computer or other processor having hardware, software, and/or firmware. The various method steps may be performed by modules, and the modules may comprise any of a wide variety of digital and/or analog data processing hardware and/or software arranged to perform the method steps described herein. The modules optionally comprising data processing hardware adapted to perform one or more of these steps by having appropriate machine programming code associated therewith, the modules for two or more steps (or portions of two or more steps) being integrated into a single processor board or separated into different processor boards in any of a wide variety of integrated and/or distributed processing architectures. These methods and systems will often employ a tangible media embodying machine-readable code with instructions for performing the method steps described above. Suitable tangible media may comprise a memory (including a volatile memory and/or a non-volatile memory), a storage media (such as a magnetic recording on a floppy disk, a hard disk, a tape, or the like; on an optical memory such as a CD, a CD-R/W, a CD-ROM, a DVD, or the like; or any other digital or analog storage media), or the like. While the exemplary embodiments have been described in some detail, by way of example and for clarity of understanding, those of skill in the art will recognize that a variety of modification, adaptations, and changes may be employed.

The methods and apparatuses of the present invention may be provided in one or more kits for such use. The kits may comprise a system for determining a treatment for an eye of a patient, and instructions for use. Optionally, such kits may further include any of the other system components described in relation to the present invention and any other materials or items relevant to the present invention. The instructions for use can set forth any of the methods as described herein.

While the above provides a full and complete disclosure of exemplary embodiments of the present invention, various modifications, alternate constructions and equivalents may be employed as desired. Consequently, although the embodiments have been described in some detail, by way of example and for clarity of understanding, a variety of modifications, changes, and adaptations will be obvious to those of skill in the art. Accordingly, the above description and illustrations should not be construed as limiting the invention, which can be defined by the claims.

What is claimed is:

1. A method of evaluating a vision treatment protocol, the method comprising:
   obtaining the vision treatment protocol;
   obtaining a random eye generator comprising a first optical parameter, wherein the random eye generator has a Rayleigh distribution for the first optical parameter; and
   evaluating the vision treatment protocol using the random eye generator.

2. The method according to claim 1, wherein the first optical parameter comprises a member selected from the group consisting of a manifest refractive sphere parameter and a wavefront sphere parameter.

3. The method according to claim 1, wherein the first optical parameter comprises the wavefront sphere parameter, and wherein the wavefront sphere parameter is based on a manifest refractive sphere parameter having a Rayleigh distribution plus a random number parameter having a normal distribution.

4. The method according to claim 1, wherein the random eye generator further comprises a second optical parameter, and wherein the random eye generator has a normal distribution for the second optical parameter.

5. The method according to claim 4, wherein the second optical parameter comprises a member selected from the group consisting of a manifest refractive cylinder parameter, a wavefront cylinder parameter, a keratometry parameter, a pachymetry parameter, a wavefront diameter parameter, and a high order aberration parameter.

6. The method according to claim 4, wherein the second optical parameter comprises a wavefront cylinder parameter, and wherein the wavefront cylinder parameter is based on a manifest refractive cylinder parameter having a normal distribution plus a random number parameter having a normal distribution.

7. The method according to claim 1, wherein the random eye generator further comprises second optical parameter, and wherein the random eye generator has a uniform distribution for the second optical parameter.

8. The method according to claim 7, wherein the second optical parameter comprises a member selected from the group consisting of a manifest refractive cylinder axis parameter and a wavefront cylinder axis parameter.

9. The method according to claim 7, wherein the second optical parameter comprises a wavefront cylinder parameter, and wherein the wavefront cylinder parameter is based on a manifest refractive cylinder parameter having a uniform distribution plus a random number parameter having a normal distribution.

10. The method according to claim 1, further comprising verifying the vision treatment protocol based on the evaluation.

11. A method of modifying a vision treatment protocol, the method comprising:
obtaining the vision treatment protocol,
obtaining a random eye generator comprising a first optical parameter, wherein the random eye generator has a Rayleigh distribution for the first optical parameter, and
modifying the vision treatment protocol using the random eye generator.

12. A system for evaluating a vision treatment protocol, comprising:
a processor;
a first module comprising a tangible medium embodying machine-readable code executed on the processor to receive the vision treatment protocol;
a second module comprising a tangible medium embodying machine-readable code executed on the processor to receive a random eye generator comprising a first optical parameter, wherein the random eye generator has a Rayleigh distribution for the first optical parameter; and
a third module comprising a tangible medium embodying machine-readable code executed on the processor to evaluate the vision treatment protocol using the random eye generator.

13. The system according to claim 12, further comprising a fourth module comprising a tangible medium embodying machine-readable code executed on the processor to verify the vision treatment protocol based on the evaluation.

14. The system according to claim 12, wherein the first optical parameter comprises a member selected from the group consisting of a manifest refractive sphere parameter and a wavefront sphere parameter.

15. The system according to claim 12, wherein the first optical parameter comprises the wavefront sphere parameter, and wherein the wavefront sphere parameter is based on a manifest refractive sphere parameter having a Rayleigh distribution plus a random number parameter having a normal distribution.

16. The system according to claim 12, wherein the random eye generator further comprises a second optical parameter, and wherein the random eye generator has a normal distribution for the second optical parameter.

17. The system according to claim 16, wherein the second optical parameter comprises a member selected from the group consisting of a manifest refractive cylinder parameter, a wavefront cylinder parameter, a keratometry parameter, a pachymetry parameter, a wavefront diameter parameter, and a high order aberration parameter.

18. The system according to claim 16, wherein the second optical parameter comprises a wavefront cylinder parameter, and wherein the wavefront cylinder parameter is based on a manifest refractive cylinder parameter having a normal distribution plus a random number parameter having a normal distribution.

19. The system according to claim 12, wherein the random eye generator further comprises second optical parameter, and wherein the random eye generator has a uniform distribution for the second optical parameter.

20. The system according to claim 19, wherein the second optical parameter comprises a member selected from the group consisting of a manifest refractive cylinder axis parameter and a wavefront cylinder axis parameter.

21. A method of evaluating a vision treatment protocol, the method comprising:
receiving, at a processor system, the vision treatment protocol; and
executing, using the processor system, computer executable code stored on a non transitory computer readable medium, the computer executable code comprising instructions to evaluate the vision treatment protocol using a random eye generator, wherein the random eye generator comprises a first optical parameter, and wherein the random eye generator has a Rayleigh distribution for the first optical parameter.

22. The method according to claim 21, wherein the first optical parameter comprises a member selected from the group consisting of a manifest refractive sphere parameter and a wavefront sphere parameter.

23. A method of modifying a vision treatment protocol, the method comprising:
receiving, at a processor system, the vision treatment protocol; and
executing, using the processor system, computer executable code stored on a non transitory computer readable medium, the computer executable code comprising instructions to modify the vision treatment protocol using a random eye generator, wherein the random eye generator comprises a first optical parameter, and wherein the random eye generator has a Rayleigh distribution for the first optical parameter.

24. The method according to claim 23, wherein the first optical parameter comprises a member selected from the group consisting of a manifest refractive sphere parameter and a wavefront sphere parameter.

* * * * *